(12) United States Patent
Zheleznyak et al.

(10) Patent No.: US 11,612,479 B2
(45) Date of Patent: Mar. 28, 2023

(54) VISION CORRECTION WITH LASER REFRACTIVE INDEX CHANGES

(71) Applicant: University of Rochester, Rochester, NY (US)

(72) Inventors: Leonard Zheleznyak, Pittsford, NY (US); Scott Catlin, Pittsford, NY (US)

(73) Assignee: University of Rochester, Rochester, NY (US)

( * ) Notice: Subject to any disclaimer, the term of this patent is extended or adjusted under 35 U.S.C. 154(b) by 204 days.

(21) Appl. No.: 17/188,220

(22) Filed: Mar. 1, 2021

(65) Prior Publication Data

US 2021/0177578 A1 Jun. 17, 2021

Related U.S. Application Data

(62) Division of application No. 15/892,987, filed on Feb. 9, 2018, now Pat. No. 10,932,901.

(60) Provisional application No. 62/457,630, filed on Feb. 10, 2017.

(51) Int. Cl.
| | |
|---|---|
| *A61F 2/16* | (2006.01) |
| *A61F 2/14* | (2006.01) |
| *G02B 1/04* | (2006.01) |
| *A61F 9/008* | (2006.01) |
| *G02C 7/04* | (2006.01) |
| *H01S 3/22* | (2006.01) |

(52) U.S. Cl.
CPC .......... *A61F 2/1618* (2013.01); *A61F 2/1451* (2015.04); *A61F 2/1613* (2013.01); *A61F 2/1651* (2015.04); *A61F 2/1654* (2013.01); *A61F 9/00806* (2013.01); *A61F 9/00812* (2013.01); *A61F 9/00825* (2013.01); *A61F 9/00827* (2013.01); *A61F 9/00829* (2013.01); *A61F 9/00834* (2013.01); *A61F 9/00838* (2013.01); *G02B 1/043* (2013.01); *G02C 7/041* (2013.01); *G02C 7/049* (2013.01); *A61F 2002/1696* (2015.04); *A61F 2009/0087* (2013.01); *A61F 2009/00842* (2013.01); *A61F 2009/00848* (2013.01); *A61F 2009/00872* (2013.01); *A61F 2009/00895* (2013.01); *A61F 2250/0053* (2013.01); *G02C 7/048* (2013.01); *G02C 2202/12* (2013.01); *G02C 2202/22* (2013.01); *G02C 2202/24* (2013.01); *H01S 3/2222* (2013.01)

(58) Field of Classification Search
CPC .... A61F 2/1618; A61F 2/1451; A61F 2/1651; A61F 2/1613; A61F 2/1654; A61F 9/00806; A61F 9/00812; A61F 9/00825; A61F 9/00827; A61F 9/00829; A61F 9/00834; A61F 9/00838; G02B 1/043; G02C 7/041; G02C 7/049
USPC .................................................... 351/159.07
See application file for complete search history.

(56) References Cited

U.S. PATENT DOCUMENTS

| | | | | |
|---|---|---|---|---|
| 5,378,582 A | * | 1/1995 | Chan ................. | B23K 26/0734 |
| | | | | 351/159.01 |
| 5,997,140 A | * | 12/1999 | Zhang .................... | G02C 7/06 |
| | | | | 430/1 |
| 6,089,711 A | * | 7/2000 | Blankenbecler ....... | G02C 7/041 |
| | | | | 351/159.02 |

(Continued)

*Primary Examiner* — James R Greece

(57) ABSTRACT

Methods and systems wherein laser induced refractive index changes by focused femtosecond laser pulses in optical polymeric materials or optical tissues is performed to address various types of vision correction.

18 Claims, 15 Drawing Sheets

(56) References Cited

U.S. PATENT DOCUMENTS

| | | | | |
|---|---|---|---|---|
| 6,139,146 A * | 10/2000 | Zhang | ................... | G02C 7/041 |
| | | | | 351/159.22 |
| 6,139,147 A * | 10/2000 | Zhang | ................... | G02C 7/043 |
| | | | | 264/1.36 |
| 7,025,460 B2 * | 4/2006 | Smitth | ................... | G02C 7/04 |
| | | | | 351/205 |
| 9,541,772 B2 * | 1/2017 | De Sio | ................. | A61F 2/1624 |
| 2013/0050712 A1 * | 2/2013 | Samukawa | .......... | G01M 11/025 |
| | | | | 356/612 |

* cited by examiner

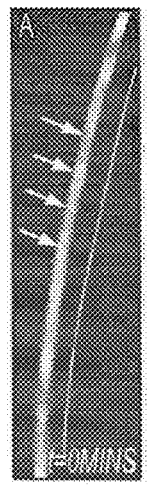 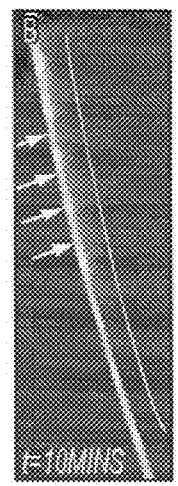
FIG. 5A  FIG. 5B
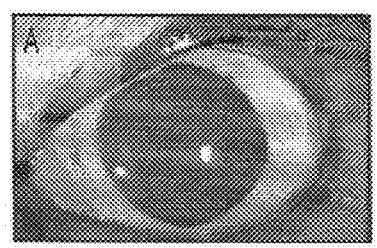
FIG. 6A
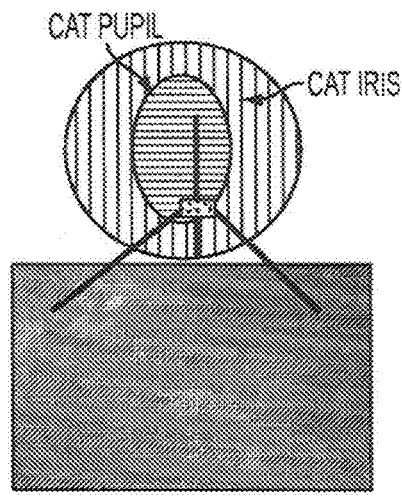
FIG. 6B
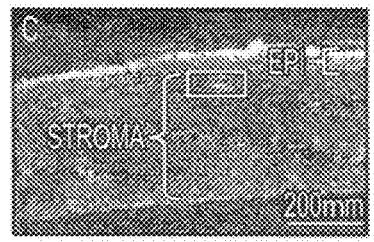
FIG. 6C

VISION CORRECTION WITH LASER REFRACTIVE INDEX CHANGES

CROSS REFERENCE TO RELATED APPLICATIONS

This application is a divisional of copending U.S. Ser. No. 15/892,987 filed Feb. 9, 2018, which claims the benefit under 35 USC 119(e) of Provisional Patent Application No. 62/457,630 filed Feb. 10, 2017, the disclosures of which are hereby incorporated by reference herein in their entireties.

FIELD OF THE INVENTION

The present disclosure is directed to vision correction and more particularly to vision correction by modifying the index of refraction of optical polymeric lens material or of ocular tissue in the eye by a high-repetition, low-pulse energy femtosecond laser.

BACKGROUND

U.S. Publication No. 2008/0001320, the disclosure of which is incorporated herein by reference in its entirety, describes methods for modifying the refractive index of optical polymeric materials, such as intraocular lenses or contact lenses, using very short pulses from a visible or near-IR laser having a pulse energy from 0.5 nJ to 1000 nJ, where the intensity of light is sufficient to change the refractive index of the material within the focal volume, whereas portions just outside the focal volume are minimally affected by the laser light. Irradiation within the focal volume results in refractive optical structures characterized by a positive change in refractive index of 0.005 or more relative to the index of refraction of the bulk (non-irradiated) polymeric material. Under certain irradiation conditions and in certain optical materials, a change in refractive index of 0.06 was measured. In general, there are two types of intraocular lenses, referred to as pseudo-phakic IOLs and phakic IOLs. The former type replaces the eye's natural, crystalline lens, usually to replace a cataractous lens that has been removed. The latter type is used to supplement an existing lens and functions as a permanent corrective lens, which is implanted in the anterior or posterior chamber to correct refractive errors of the eye. The change in refractive index can be used to form patterned desired refractive structures in the optical polymeric material.

As opposed to modifying the refractive index in ophthalmic lenses such as intraocular lenses or contact lenses, U.S. Pat. No. 8,512,320, the disclosure of which is incorporated herein by reference in its entirety, discloses a method for correcting vision in a patient by modifying the refractive index of ocular tissue itself, such as cornea tissue or natural crystalline lens tissue. The method comprises identifying and measuring the degree of vision correction of the patient; and determining the position and type of refractive structures to be written into the cornea tissue of the patient to correct the patient's vision. The refractive structures are written by irradiating select regions of the cornea tissue with focused laser pulses having a wavelength in the visible or near-IR, e.g., from 400 nm to 900 nm, and a pulse energy from 0.01 nJ to 10 nJ. The refractive structures are characterized by a positive change in refractive index in relation to non-irradiated cornea tissue of the patient. Such process may be referred to as Intra-tissue Refractive Index Shaping (IRIS) in biological tissues or Intra-Polymer Refractive Index Shaping (IRIS) in optical polymers, such as intraocular lenses, contact lenses or corneal inlays.

U.S. Publication No. 2012/0310340, the disclosure of which is incorporated herein by reference in its entirety, describes a method for providing changes in refractive power of an optical device made of an optical, polymeric material by forming at least one laser-modified, gradient index (GRIN) layer disposed between an anterior surface and a posterior surface of the device by scanning with light pulses from a visible or near-IR laser along regions of the optical, polymeric material. The at least one laser-modified GRIN layer comprises a plurality of adjacent refractive segments, and is further characterized by a variation in index of refraction of at least one of: (i) a portion of the adjacent refractive segments transverse to the direction scanned; and (ii) a portion of refractive segments along the direction scanned. U.S. Publication 2012/0310223, the disclosure of which is incorporated herein by reference in its entirety, discloses a method of modifying the refractive index in ocular tissues wherein a laser-modified gradient index (GRIN) layer is formed directly in at least one of the corneal stroma and the crystalline lens.

In such processes, the irradiated regions of the optical tissue or optical polymeric material can take the form of two- or three-dimensional, area or volume filled refractive structures. The refractive structures are formed by scanning the laser over a select region of the optical tissue or polymeric material resulting in refractive optical structures that can provide spherical, aspherical, toroidal, or cylindrical correction to the optical tissue or a polymeric lens. In fact, any optical structure can be formed to yield positive or negative power corrections. Moreover, the optical structures can be stacked vertically or written in separate planes in optical tissue or the polymeric material to act as a single lens element.

There is an ongoing need for new and improved techniques and materials, and refractive corrector vision components resulting therefrom, for improving human vision. Such components may include IOLs for use following cataract surgery, or may be in the form of corneal inlays or other implantable vision correction devices, or contact lenses. There are also advantages and benefits that would result from such techniques and components allowing in-situ modification of refractive properties (e.g., refractive index, dioptric power) of such components, as well as direct modification of ocular tissue to provide corrected vision.

SUMMARY

The present disclosure is directed towards various methods and systems wherein laser induced refractive index changes by focused femtosecond laser pulses in optical polymeric materials or optical tissues is performed to address various types of vision correction.

One embodiment of the disclosure is directed towards an optical device selected from a contact lens, intraocular lens, or corneal inlay for improving visual performance in a patient, including central optical and outer peripheral zones comprising an optical polymer material, wherein select regions of the optical device in the central and outer zones have been irradiated with a focused, visible or near-IR laser below the optical breakdown threshold of the optical polymer material to provide refractive structures that exhibit a change in refractive index, and exhibit little or no scattering loss, and wherein ablation or removal of the optical polymeric material is not observed in the irradiated regions, wherein laser-irradiated refractive structures provided in the central optical zone of the optical device provide one or more of the following when the optical device is employed by a patient: extended depth of focus by inducing a higher order aberration; diffractive multifocal; refractive multifocal; chromatic aberration correction; higher order aberration corrections; binocular monovision; rotationally symmetric or asymmetric single ring; or custom corrections; and further wherein laser-irradiated refractive structures provided in the peripheral zone of the optical device provide a region of altered refractive index to reduce glare, halo, edge effects or dysphotopsias.

Another embodiment of the disclosure is directed towards an optical contact lens including central optical and outer peripheral zones comprising an optical polymer material, wherein select regions of the optical device have been irradiated with a focused, visible or near-IR laser below the optical breakdown threshold of the optical polymer material to provide refractive structures that exhibit a change in refractive index, and exhibit little or no scattering loss, and wherein ablation or removal of the optical polymeric material is not observed in the irradiated regions, and wherein the outer peripheral zone includes stabilization features to maintain orientation of the contact lens relative to a user's eye.

Another embodiment of the disclosure is directed towards a method for modifying an optical device selected from a contact lens, intraocular lens, or corneal inlay for improving visual performance in a patient, wherein the optical device includes central optical and outer peripheral zones comprising an optical polymer material, comprising: modifying the refractive index of the optical polymer material in the central and outer peripheral zones by irradiating select regions with a focused, visible or near-IR laser below the optical breakdown threshold of the optical polymer material to provide refractive structures that exhibit a change in refractive index, and exhibit little or no scattering loss, and scanning over the select regions with the laser such that ablation or removal of the optical polymer material is not observed in the irradiated region; wherein refractive structures provided in the central optical zone of the optical device provide one or more of the following when the optical device is employed by a patient: extended depth of focus by inducing a higher order aberration; diffractive multifocal; refractive multifocal; chromatic aberration correction; higher order aberration corrections; binocular monovision; rotationally symmetric or asymmetric single ring; or custom corrections; and further wherein refractive structures provided in the peripheral zone of the optical device provide a region of altered refractive index to reduce glare, halo, edge effects or dysphotopsias.

Another embodiment of the disclosure is directed towards a method for improving binocular visual performance in a presbyopia patient, comprising: modifying the refractive index of ocular tissue of an eye of the patient, by irradiating select regions of the ocular tissue with a focused, visible or near-IR laser below the optical breakdown threshold of the tissue to provide refractive structures that exhibit a change in refractive index, and exhibit little or no scattering loss, and scanning over the select regions with the laser such that ablation or removal of the tissue is not observed in the irradiated region, wherein the refractive structures provided include one or more of the following: extended the depth of focus by inducing a higher order aberration to the patient's eye; diffractive multifocal; refractive multifocal; chromatic aberration correction; higher order aberration corrections; binocular monovision; rotationally symmetric or asymmetric single ring; or custom corrections.

Another embodiment of the disclosure is directed towards a method for providing an intraocular telescope lens system in an eye, comprising: modifying the refractive index of crystalline lens tissue of the eye by irradiating select regions of the crystalline lens tissue with a focused, visible or near-IR laser below the optical breakdown threshold of the crystalline lens tissue to provide a negative power lens element in the crystalline lens that exhibits a change in refractive index relative to non-irradiated crystalline lens tissue, and exhibits little or no scattering loss, and scanning over the select regions with the laser such that ablation or removal of the tissue is not observed in the irradiated region, and modifying the refractive index of cornea tissue of the eye by irradiating select regions of the cornea tissue with a focused, visible or near-IR laser below the optical breakdown threshold of the cornea tissue to provide a positive power lens element in the cornea that exhibits a change in refractive index relative to non-irradiated cornea tissue, and exhibits little or no scattering loss, and scanning over the select regions with the laser such that ablation or removal of the tissue is not observed in the irradiated region, and wherein the negative and positive power lens elements are aligned along an optical axis in the eye.

Another embodiment of the disclosure is directed towards a method for providing an intraocular telescope lens system in an eye, comprising: inserting an intraocular lens comprising a negative power lens element in the eye, and modifying the refractive index of cornea tissue of the eye by irradiating select regions of the cornea tissue with a focused, visible or near-IR laser below the optical breakdown threshold of the cornea tissue to provide a positive power lens element in the cornea that exhibits a change in refractive index relative to non-irradiated cornea tissue, and exhibits little or no scattering loss, and scanning over the select regions with the laser such that ablation or removal of the tissue is not observed in the irradiated region, and wherein the negative and positive power lens elements are aligned along an optical axis in the eye.

Another embodiment of the disclosure is directed towards a method for placing myopic hyperopic defocus on the peripheral retina of an eye to prevent or slowing myopia progression in a patient, comprising: modifying the refractive index of ocular tissue of an eye of the patient, or of an optical device selected from an intraocular lens, contact lens, or corneal inlay, by irradiating select regions of the ocular tissue or optical device material with a focused, visible or near-IR laser below the optical breakdown threshold of the tissue or optical device material to provide refractive structures that exhibit a change in refractive index, and exhibit little or no scattering loss, and scanning over the select regions with the laser such that ablation or removal of the tissue or optical device material is not observed in the irradiated region, wherein the refractive structures provided form at least one peripheral zone having a different dioptric power around a center zone of the cornea or natural crystalline lens, or of an intraocular lensoptical device, so as to provide a multifocal power profile in the cornea or natural crystalline lens, or optical device.

In the various embodiments of the disclosure, one or more of the following features may be employed alone or in combination: the focused, visible or near-IR laser has a pulse energy from 0.01 nJ to 10 nJ; a multiple-photon-absorbing chromophore may be applied to the optical tissue prior to modifying the refractive index of the ocular tissue; the multiple-photon-absorbing chromophore comprises a two-photon-absorbing chromophore; the ocular tissue comprises tissue of a lens; the ocular tissue comprises tissue of a cornea; locations defined by the focus spot are selected to form a structure selected from the group consisting of Bragg gratings, microlens arrays, zone plates, and Fresnel lenses; the laser pulses are emitted at a frequency between 1 MHz and 10 GHz; the laser frequency is between 10 MHz and 500 MHz; the pulse width is between 10 fs and 100 fs; the laser pulses have an average power between 1 mW and 1,000 mW; the laser pulses have a pulse energy between 0.01 nJ and 10 nJ; the laser pulses have a pulse energy between 0.1 and 2 nJ; the size of the focus spot is between 0.5 micrometer and 2 micrometer; the focus spot is scanned at a scanning speed between 0.1 micrometer/s and 100 mm/s; the focus spot is scanned at a scanning speed of at least 1 mm/s; the focus spot is scanned at a scanning speed of at least 100 mm/s; the laser pulses have a wavelength between 600 and 1,000 nm; the wavelength is between 700 and 900 nm; the laser pulses have a wavelength between 1,000 and 1,300 nm; the laser pulses have a wavelength between 350 and 600 nm.

BRIEF DESCRIPTION OF THE DRAWINGS

FIGS. 5A and 5B show slit lamp imaging of the cornea, showing the penetration of a chromophore;

FIGS. 6A-6C show IRIS in the unfixed cat cornea;

DETAILED DESCRIPTION

Figure 1A:
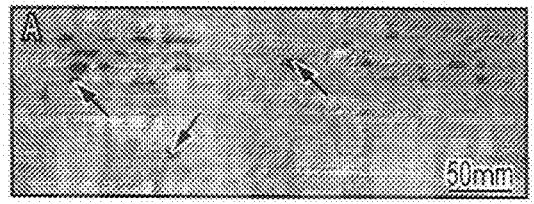
FIGS. 1A-1D show femtosecond IRIS in a lightly fixed cat corneal stroma just around the tissue breakdown threshold.

Ametropia to be corrected may include, for example, myopia, hyperopia, astigmatism or presbyopia. In particular embodiments, the present disclosure relates to correcting higher-order errors of refracting power, and in particular, fourth-order errors of refracting power (spherical aberrations). Additional aberrations may also be corrected, including astigmatism, coma, trefoil, and any combination of these, as well as defocus and spherical aberrations. Further, custom correction for an individual's particular combination of aberrations and defocus may be corrected in a custom correction registered to their particular vision issues as diagnosed via wavefront abberometry, manifest refraction, topography, etc. Chromatic aberration can also be corrected using certain embodiments, for example a positive Diopter monofocal or multifocal diffractive add power may be used to counteract chromatic aberrations caused by the eye (either cornea or natural lens), contact lenses, intraocular lenses and/or corneal inlays, either individually or in combination (see for example, U.S. Pat. No. 6,830,332, which is incorporated by reference herein in its entirety for chromatic aberration corrections).

Laser Induced Refractive Index Change Description

Choosing the right laser parameters is critical for achieving IRIS in biological tissues. Not only does the femtosecond laser fluence at the objective focus have to be below the optical breakdown threshold of the tissue, it also had to be strong enough to induce some nonlinear changes, and the scan speed must be set within a specified range. In the past two decades, extensive experimental and theoretical work has been done to characterize laser-induced optical breakdown thresholds in different materials, including the cornea (Docchio, Sacchi & Marshall, 1986, Du, Liu, Korn, Squier & Mourou, 1994, Giguere et al., 2007, Loesel et al., 1996, Stern, Schoenlein, Puliafito, Dobi, Birngruber & Fujimoto, 1989, Stuart, Feit, Rubenchik, Shore & Perry, 1995, Tien, Backus, Kapteyn, Murnane & Mourou, 1999, Vogel et al., 2005) and the lens (Brazitikos, D'Amico, Bochow, Hmelar, Marcellino & Stangos, 1998, Li & Borkman, 1990, Vogel, Capon, Asiyo-Vogel & Birngruber, 1994). However, most of this work centered on the use of continuous wave (CW) lasers or on single pulses from low-repetition-rate lasers in which thermal diffusion time is much shorter than the time interval between adjacent pulses. Thus, each pulse is responsible for a change in the material. Indeed, it has been established that for pulses longer than 10 ps, the optical breakdown threshold fluence scales as the square root of the pulse duration (Du et al., 1994). For pulses shorter than 10 ps but longer than about 100 fs (which is the case with IRIS settings), the experimental results show a departure from this dependence. However, whether threshold fluence increases or decreases as pulse durations get shorter remains a challenging question (Stern et al., 1989, Stuart et al., 1995, Tien et al., 1999).

When high-repetition-rate femtosecond laser pulses are used, cumulative, free-electron-mediated chemical effects, photochemical bond breaking and thermal effects contribute to the laser-tissue interaction. As a result, the breakdown threshold fluence may be quite different from that predicted by current models (Vogel et al., 2005). Several studies on the effects of high-repetition-rate femtosecond lasers on fused silica and borosilicate glass have found that laser pulses greatly increased the temperature of the materials at the laser focus (Eaton, Zhang, Herman, Yoshino, Shah, Bovatsek & Arai, 2005a). Vogel calculated the temperature change in water would be >10° K with a 0.6NA focusing lens and 100 fs laser pulses (Vogel et al., 2005), assuming that with each pulse, an energy density of 1 $J/cm^3$ at the center of the initial temperature distribution is deposited. Using very high-repetition-rate (93 MHz), ultra-short laser pulses (27 fs), it was found that the optical breakdown threshold for the 0.70NA focusing condition in lightly-fixed corneal stroma and lens cortex to be 55 mW and 75 mW average laser power respectively (Ding et al., 2008). This corresponds to 0.6 nJ and 0.8 nJ pulse energies respectively, both lower than the optical breakdown power reported by König and colleagues using 1 nJ pulse energy, 170 fs pulse duration and 1.30NA focusing in porcine corneas (König et al., 2002). By using 30 mW and 45 mW average laser power (0.3 nJ and 0.5 nJ pulses), it was able to induce IRIS, without accompanying photo-disruption and tissue destruction.

Experiments demonstrated that it is possible to cause low-scattering-loss, refractive index modifications in lightly-fixed cat cornea and lens using 93 MHz repetition rate, 27 fs laser pulses with 0.3 nJ and 0.5 nJ pulse energies. These modifications were visible only using DIC microscopy and were not associated with apparent tissue damage. They represent refractive index changes between 0.005±0.001 and 0.021±0.001. Preservation of IRIS over a month of refrigerated storage suggested that the femtosecond laser-induced modifications were likely to involve relatively long-term molecular/structural alterations. In related experiments involving silicone hydrogels, the micromachined gratings (and associated Raman spectra) were observed to persist for up to one year, even after drying and rehydration of the hydrogel (Ding, Cancado, Novotny, Knox, Anderson, Jani, Blackwell, Künzler & Smith).

Even relatively small refractive index changes induced in cornea and lens tissue can have a significant impact on optical power. Based on published values for the power (39D) and native refractive index (1.376) of the cat cornea (Hughes, 1977), IRIS should generate a change in corneal power ranging between 0.14D and 0.56D (assuming an index change between 0.005 and 0.02). Similarly, for the cat lens (power=53D, refractive index of the homogeneous lens=1.554) (Hughes, 1977), the refractive index changes induced by micromachining should theoretically alter lenticular power by between 0.5D and 0.7D. The ultimate change in power is based on both the change in refractive index and the optical path length over which the refractive index is changed. In other words, the total refractive change is the change in refractive index multiplied times the length of the changed portion of the material. As such, even small changes over a longer path length can have significant refractive power, or a large refractive index change over a small path length could have a significant refractive power.

Improvement in refractive index change and/or writing speeds may be achieved by employing a laser wavelength in a range for which the optical tissue is more inherently sensitive to 2-photon absorption. US 20110071509, the disclosure of which is incorporated herein by reference in its entirety, e.g., discloses more particularly a method for forming a refractive structure in a living eye, where the method includes the steps of directing and focusing a plurality of femtosecond laser pulses in a spectral region between about 350 nanometers (nm) to about 600 nm, and more particularly blue light, within a cornea or a lens of the living eye; controlling the intensity of the laser pulses to have an intensity sufficient to change the refractive index of the cornea or lens within a defined focal region, but below a damage threshold the cornea or lens, or at a level that will not photo-disrupt cornea or lens tissue outside of the focal region; and forming a refractive structure in the focal region of the cornea or the lens by scanning the laser pulses through a volume of the cornea or the lens. Each refractive structure is characterized by a change in refractive index, and exhibits little or no scattering loss.

Additionally or alternatively, a photosensitizer may be employed to chemically enhance the two-photon absorption properties of both tissues. Such photosensitization can result in an increase in (for example, at least a doubling of) the refractive index changes and an increase in laser writing speed (for example, greater than a 10× increase or even a several hundred fold increase in the micromachining speeds attained). The use of a photosensitizer is more specifically disclosed in U.S. Pat. No. 9,545,340, the disclosure of which is incorporated by reference herein in its entirety. Some multiphoton or two-photon absorbers may include fluorescein, coumarin, acetaminophen or riboflavin.

Ongoing experiments have generated information about the cellular and molecular mechanisms underlying IRIS in the living cornea, allowing us to gain critical knowledge that can be used to further manipulate the size, placement and design of micromachined patterns, as well as the magnitude of the refractive index changes with which they are associated. The ability to alter the native refractive index of the cornea and lens without causing significant tissue damage has important theoretical and practical implications. By understanding how laser power can be used to alter tissues non-destructively, and by understanding the nature of these alterations, we could open up an entirely new branch in the field of laser biology. Among other things, this could completely change our approach to laser refractive surgery, and to vision correction more generally. For instance, the preservation of tissue clarity during the treatment allows the application of IRIS for the creation of corneal fiducial markings that could be used to align eye trackers during LASIK, and for refractive corrections in a closed-loop approach, e.g. with specific benefit for the correction of higher-order aberrations, as well as for "touch-up corrections" of ocular surface defects. More broadly, the feasibility of IRIS in living tissues offers new possibilities for non-invasive alterations, marking or pattern-inscription within living organisms. From a theoretical stand-point, it also provides a unique opportunity to better understand and define the extent to which we can optically manipulate even large areas of living tissues without inducing a significant wound healing reaction.

Various ranges of parameters are particularly useful in implementing IRIS in the present disclosure. In treatment of the eye, the laser wavelength should be such that the tissues through which laser pulses pass are transparent to the pulses—for example, 350 nm-1600 nm, or more preferably 400 nm-1100 nm. There should also be limited or no damage to the retina; any significant change should be confined to the tissue located at the spot of focus of the pulses.

A laser pulse frequency (repetition rate) of 93 MHz is useful for many applications, as is a repetition rate of between 10 MHz and 100 MHz. A preferable range is from 1 MHz to 10 GHz, and more preferably from 10 to 500 MHz.

Linked to the pulse frequency is the average power. A preferable range is from 1 to 1,000 mW, and more preferably 10 to 100 mW, and more preferably still from 50 to 60 mW. The energy of each pulse should preferably be less than 1 nJ and more preferably less than 0.5 nJ, although a range from 0.01 to 10 nJ and more preferably from 0.1 to 2 nJ can be used.

A laser pulse width of 30 fs is useful for many applications. A preferable range is from 5 fs to 1 ps, more preferably from 10 to 300 fs, and more preferably from 30 to 200 fs.

The scanning speed of the laser is preferably at least 0.4 µm/s, more preferably at least 0.1 mm/s, or at least 1 mm/s or at least 10 mm/s, and more preferably greater than 50 mm/s and higher. For example, scan speeds of 100 mm/s, 200 mm/s, 400 mm/s and up to 700 mm/s and even higher and all speeds in between are valuable and many have been demonstrated and are effective to reduce the treatment time. Apparatus which may be employed in the present disclosure and which is capable of obtaining such high scanning speeds is described, e.g., in WO 2015/006274, the disclosure of which is incorporated by reference herein in its entirety.

The wavelength should be one to which the tissues through which the laser pulses must pass are transparent. It should also preferably be just barely within the visible range for the patient (e.g., around 400 nm, or from 375 nm to 425 nm), within the visible range (e.g., 400 nm-750 nm), or outside of the visible range (e.g., near-infrared), so as not to bother the patient. In the near-infrared range, a wavelength of 800 nm is useful, as is a wavelength of 1000-1040 nm. Further preferable ranges include 600-1,000 nm (and more preferably 700-900 nm) and above 1,000 nm (e.g., 1000-1300 nm).

The laser pulses are focused to a cross-sectional spot size that is preferably 1 μm. Preferable ranges include 0.5 μm to 2, 10, or 50 μm. Further the spot length along the z-axis (i.e. length or depth along the axis of the laser beam) may be of similar dimensions or different to those for the cross-sectional spot size. For example, the spot length along the z-axis may be in the range of 1-50 microns, or preferably from 1-20 microns.

Various structures can be produced in the ocular tissue as well as polymers for optical lenses, such as contacts, intraocular lenses and corneal inlays. Examples include high refractive index structures such as Bragg gratings, microlens arrays, optical zone plates, diffraction patterns and Fresnel lenses, as well as a variety of refractive lenses and refractive multifocals.

Embodiments of IRIS will now be set forth in detail with reference to the drawings.

Preliminary experiments (Ding, Huxlin & Knox, 2007, Ding et al., 2008, Huxlin, Ding & Knox, 2008) showed that it is possible to change the refractive index of the lightly-fixed, mammalian cornea and lens without tissue destruction, a phenomenon termed Intra-tissue Refractive Index Shaping (IRIS). To achieve this, first measured, then reduced femtosecond laser pulse energies below the optical breakdown threshold of lightly-fixed post-mortem cat corneas and lenses. In both silicone and non-silicone-based hydrogels, this approach induced a significant change in refractive index without visible plasma luminescence or bubble formation (Ding et al., 2006).

Eight corneas and eight lenses were extracted under surgical anesthesia from five normal, adult domestic shorthair cats (*Felis cattus*). To avoid decomposition and opacification prior to femtosecond laser micromachining, extracted feline tissues were immediately drop-fixed for 10 minutes (corneas) or one hour (lenses) in a solution consisting of 1% paraformaldehyde in 0.1M phosphate buffered saline (PBS), pH 7.4. Lenses were then cut into 500 μm thick slices using a HM650V vibratome (Microm International), after which lens sections and whole corneas (also ~500 μm thick) were immersed in a mixture of 30% ethylene glycol+30% sucrose in 0.1M PBS, pH7.4 at 4° C. Storage in this solution minimized tissue swelling and loss of transparency. Small pieces of tissue, ~1 cm² were then flattened onto a clear glass slide (1×3 inches, 1 mm thick, Surgipath Medical Industries Inc., IL). In the case of corneal pieces, this was done with the epithelium facing up and the endothelium facing down. A glass coverslip (Corning No. 0211 Zinc Titania glass) was placed on the top of each piece, stabilizing it for the duration of the experiment. The ethylene glycol/ sucrose storage solution was used as mounting medium to minimize dehydration of the cornea and lens tissue samples since these effects are known to alter the refractive index and transparency of both these tissues (Fisher, Masiello, Goldstein & Hahn, 2003, Meek, Dennis & Khan, 2003, Patel, Alio & Perez-Santonja, 2004).

Femtosecond laser micro-machining was conducted as previously described in hydrogels (Ding et al., 2006). The laser source was a Kerr-lens mode-locked Ti:Sapphire laser (K-M Labs). The laser oscillator generated pulses averaging 300 mW, 27 fs in duration, with a 93 MHz repetition rate at 800 nm wavelength. A continuously variable, metallic, neutral density filter inserted into the optical path, was used to adjust the incident laser power onto each cat cornea and lens piece. Pulses were focused 100 μm below the tissue surface using a 60×, 0.70NA Olympus LUCPlanFLN microscope objective with an adjustable working distance of 1.5-2.2 mm. Because the large amount of glass within the microscope objective induced significant chromatic dispersion into the femtosecond laser pulses, broadening the pulse durations, a standard extra-cavity-prism double-pass configuration was used to compensate for the dispersion and maintain the ultra-short pulse duration. By carefully adjusting this dispersion compensator, nearly transform-limited 27 fs duration pulses were obtained at the focal point of the focusing objective, as measured by a collinear auto-correlator using 3rd order surface harmonic generation (Meschulach, Barad & Silberberg, 2003, Squier, Fittinghoff, Barty, Wilson, Muller & Brakenhoff, 1998). During IRIS, the slide containing the biological tissue samples was mounted on a 3D scanning platform consisting of a Physik Instrumente P-622.2CD XY scanning stage with 250 μm travel range and 0.7 nm close-loop resolution, and a Newport VP-25XA linear servo Z-axis scanning stage with 25 mm travel range and 100 nm resolution. An infrared CCD camera was used to monitor the micromachining process and the generation of visible plasma luminescence in real-time.

A first step was to establish thresholds for the optical breakdown of lightly-fixed feline cornea and lens. The neutral density filter was first adjusted to minimize the focused incident laser power on the cornea and the lens below their breakdown thresholds (Giguere et al., 2007, Loesel et al., 1996). Adjusting the neutral density filter then progressively increased the incident laser power. The breakdown threshold power was reached when visible plasma luminescence suddenly appeared and strong scattering light as well as laser-induced damage became visible (FIGS. 1A-1D). With a 0.70NA long-working-distance objective, the measured breakdown thresholds for cat cornea and lens were ~55 mW and 75 mW average laser power respectively, which corresponds to pulse energies of 0.6 nJ and 0.8 nJ.

FIGS. 1A-1D: Femtosecond IRIS in lightly-fixed cat corneal stroma just around the tissue breakdown threshold. 1A,1C: Differential interference contrast (DIC) images of lines created in the stroma of two different, lightly-fixed cat corneas with 0.6 nJ pulses and a scanning speed of 10 μm/s. Note dark spots of tissue destruction and "bubbles" (arrowed) along the micromachined lines (clear, horizontal lines within stromal tissue). 1B,1D: Bright Field (BF) images of the corneal region in 1A,1C illustrating the visibility of dark spots of tissue destruction (arrowed) and the relative invisibility of the rest of the lines that are clearly seen under DIC conditions (see 1A,1C).

Figures 2A, 2B:
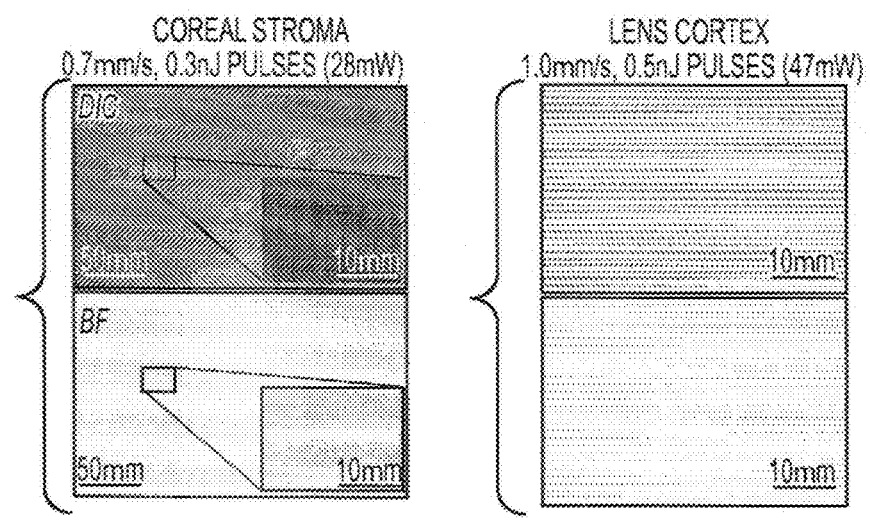
FIGS. 2A and 2B show femtosecond IRIS in a lightly fixed cat corneal stroma and lens cortex below the tissue breakdown threshold.

Once tissue breakdown thresholds were established, the focused laser power was lowered gradually by carefully adjusting the neutral density filter until lines could be micromachined without the induction of bubbles or burns (FIGS. 2A and 2B). Average laser power settings at which this could be done were 30 mW in the cornea and 45 mW in the lens, corresponding to pulse energies of about 0.3 nJ and 0.5 nJ respectively. These values lay between those used for imaging and measured breakdown thresholds. The gratings were micromachined in the horizontal plane within the stromal layer of each corneal piece and the cortex of each lens at a constant speed of 0.7 µm/s for the cornea and 1 µm/s for the lens. The spherical aberration at the laser focus induced by refractive index mismatch was compensated by adjusting the correction collar of the focusing microscope objective in order to achieve the smallest possible laser-affected region along the laser propagation direction (Ding et al., 2006).

Figure 1B:
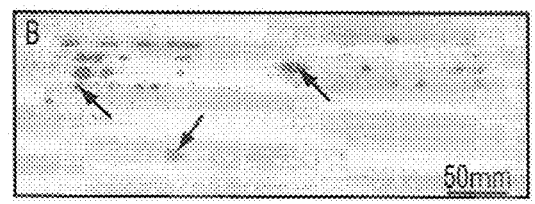
Figure 1C:
Figure 1D:
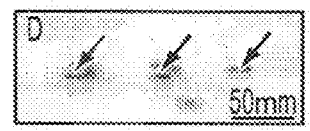

Exposure of lightly-fixed cat corneal and lenticular tissue to 0.3 nJ or 0.5 nJ femtosecond laser pulses (28 mW or 47 mW average laser power) respectively resulted in the reliable creation of line gratings about 100 µm below the epithelial surface or 100 µm below the lens surface in all test samples (FIGS. 2A and 2B). When imaged immediately after micromachining, individual grating lines could be clearly observed and distinguished with differential interference contrast (DIC) microscopy, but they were practically invisible when viewed under bright field (BF) transmission microscopy (BF images in FIGS. 2A and 2B). This could be interpreted as the grating lines having very low scattering properties, which is in contrast to the destructive tissue changes observed with laser pulse energies above the optical breakdown threshold of the tissues (FIGS. 1A-1C). Using the knife-edge method (Smith, 2000), ascertained that the laser focus diameter was 2.5 µm in air, which was much bigger than the micromachined line-widths. Thus, it appears that only the central part of the laser focal area had sufficient intensity to modify corneal and lens tissues.

FIGS. 2A and 2B: Femtosecond IRIS in lightly-fixed cat corneal stroma and lens cortex below the tissue breakdown threshold. 2A: The top photomicrographs are DIC images of a periodic line grating created using 0.3 nJ pulses and a scanning speed of 0.7 µm/s into the stromal layer of a cat corneal piece. Note the absence of tissue destruction (no brown spots). The insert shows a magnified portion of the grating. The bottom photographs are bright field (BF) images of the corneal regions shown the DIC pictures. Note the poor visibility of the micromachined gratings under transmitted, bright light microscopy, which contrasts with the high visibility of the brown spots created when using laser power above the tissue breakdown threshold (see FIGS. 1A-1C). 2B: DIC image of a periodic line grating created using 0.5 nJ pulses and a scanning speed of 1 µm/s in a piece of lens cortex. Note the absence of tissue destruction (no brown spots). The BF image shows the lens region illustrated in the DIC picture.

To assess whether the gratings generated in corneal and lens pieces were associated with a change in refractive index, the slides containing the tissue were first placed under an Olympus BX51 optical microscope where gratings were localized using DIC imaging. A low-power 632.8 nm He—Ne laser was then used to irradiate the gratings (FIGS. 3A and 3B), generating a diffraction pattern that was captured by a digital camera and used to calculate the refractive index changes attained, as described previously (Ding et al., 2006).

Figure 3A:
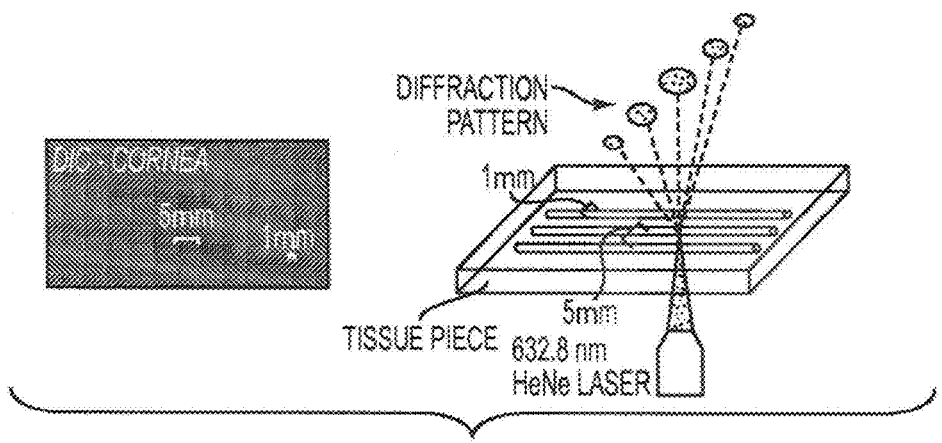
FIGS. 3A and 3B show measurement of the refractive index change in IRIS-treated corneas and lenses immediately after the treatment.
Figure 3B:
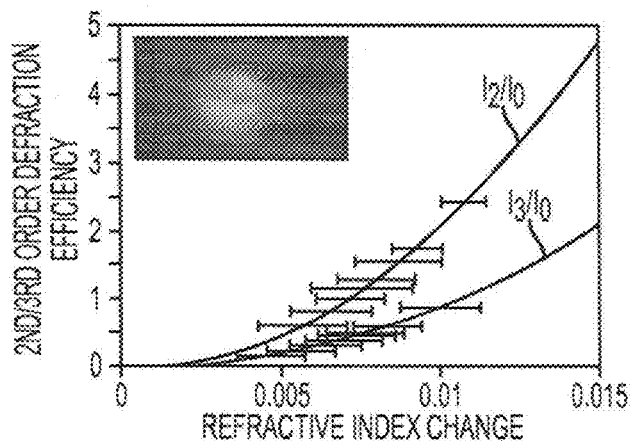

FIGS. 3A and 3B. Measuring refractive index change in IRIS-treated corneas and lenses immediately after the treatment. 3A: DIC image of a periodic line grating created using 0.3 nJ pulses and a scanning speed of 0.7 µm/s in the stromal layer of a piece of cat cornea and subsequently illuminated with a 632.8 nm He—Ne laser to generate diffraction patterns (as shown in 3B) that were used to calculate the change in refractive index attained. 3B: Graph plotting the 2nd and 3rd order diffraction efficiencies and the corresponding laser-induced refractive index changes of eight gratings micromachined in different corneal samples immediately after they were created. The insert is a photograph of the diffraction pattern obtained when illuminating the grating shown in A with a 632.8 nm He—Ne laser.

In brief, a power meter measured the intensity of the $0^{th}$-$3^{rd}$ order diffracted light from the gratings and the different order diffraction efficiencies were obtained by calculating the ratios between the intensity of the $1^{st}$, $2^{nd}$ and $3^{rd}$ to the $0^{th}$ order diffraction light. Since the intensity distribution of the diffraction pattern of a phase grating is proportional to the square value of the Fourier Transform of the transmittance function of the grating (Born & Wolf, 1970), one particular value of refractive index change matches only one particular diffraction efficiency value (Ding et al., 2006). To reduce measurement error of the diffraction order intensities, five measurements were collected on each grating, calculating the average value obtained and its standard deviation. In principle, the spatial distribution of the refractive index change within the micromachined region was a small-scale gradient-index structure. The index profile was presumed to be uniform within the grating lines, which were only 3 µm deep because the spherical aberration at the focal point was corrected (Ding et al., 2006).

Because displacement of the stromal collagen lamellae as a result of post-mortem corneal swelling could not be completely avoided the scattering effect from the $0^{th}$ order diffraction light was very strong obscuring the $1^{st}$ order diffraction light (Meek et al., 2003). Thus, only the $2^{nd}$ and $3^{rd}$ order diffraction efficiencies of each grating could be measured and used to calculate an approximate refractive index change in corneal pieces (FIG. 3B). Because tissue swelling and opacification were minimal in slices of lens cortex, the $0^{th}$ through $3^{rd}$ order diffraction light could be measured clearly and $1^{st}$ and $2^{nd}$ order diffraction efficiencies were used to calculate the induced refractive index change. Although single diffraction efficiency is usually sufficient to calculate refractive index, $1^{st}/2^{nd}$ or $2^{nd}/3^{rd}$ combinations were measured to confirm that the index changes calculated were consistent through different diffraction orders, assuming that the refractive index of cat corneal stroma and lens cortex were 1.376 and 1.400 respectively (Hughes, 1977). For corneal stroma, the index changes induced by the laser in the multiple samples ranged between 0.005±0.001 and 0.01±0.001 (FIG. 3B). For cat lens cortex, index changes were larger, ranging between 0.015±0.001 and 0.021±0.001.

After micromachining, each cornea and lens piece was stored in ethylene glycol/sucrose solution at 4° C. After one month, each piece was re-mounted onto a new glass slide for imaging and a repeat of the diffraction light intensity measurements. This allowed assessing whether the RI change initially observed had been maintained during storage. A first observation was that although the storage solution significantly slowed corneal swelling and opacification, it did not completely prevent either. In spite of this, DIC microscopy was able to reveal the grating structures initially micromachined (FIG. 4A).

Figure 4A:
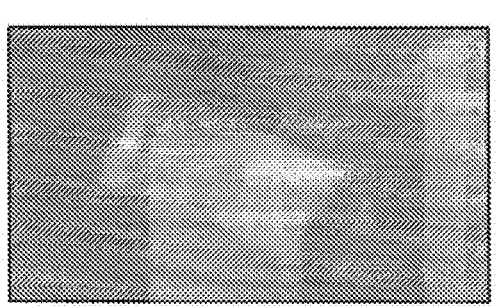
FIGS. 4A and 4B show measurement of the refractive index change in IRIS-treated corneas one month after the treatment.
Figure 4B:
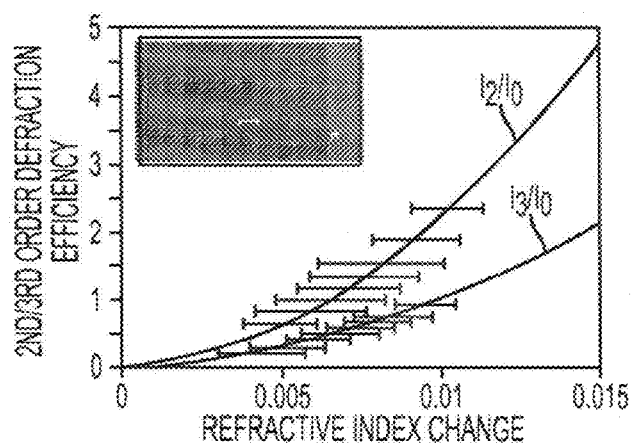

FIGS. 4A and 4B: Measuring refractive index change in IRIS-treated corneas 1 month after the treatment. 4A: DIC image of a periodic line grating created using 0.3 nJ pulses and a scanning speed of 0.7 µm/s into the stromal layer of the cat corneal piece shown in FIGS. 3A and 3B and stored for 1 month. The grating is still visible, but the clarity of its lines is decreased, a likely result of corneal swelling and opacification. 4B: Graph plotting the diffraction efficiencies and the corresponding refractive index changes of eight gratings measured one month after they were created in 8 different corneal pieces. The insert is a photograph of the diffraction pattern obtained when illuminating the grating shown in FIG. 4A with a 632.8 nm He—Ne laser.

For both corneal and lens slices, the diffraction light distribution of one-month old gratings (FIG. 4B) was not significantly different than that obtained right after the gratings' creation (FIG. 3B). In the corneal pieces, the scattering light from the $0^{th}$ order diffraction still obscured the $1^{st}$ order diffraction. However, the $2^{nd}$, $3^{rd}$ and even $4^{th}$ order diffractions were visible and measurable. In the lens pieces, the $1^{st}$, $2^{nd}$ and $3^{rd}$ order diffraction were visible. The refractive index change after one month of storage still ranged between 0.005±0.001 and 0.01±0.001 for corneal pieces and between 0.015±0.001 and 0.021±0.001 for lens slices.

IRIS can be further potentiated by increasing two-photon absorption (TPA) or other multi-photon absorption of the cornea and lens. In early work with native hydrogels, femtosecond micromachining caused index changes in the range of +0.02 to +0.06, with very slow scanning speeds, as slow as 0.4 microns per second (Ding et al., 2006). The index changes attained in the cat cornea were small (~0.005-0.01) and background scattering made the features difficult to detect. Larger index changes were written in 500 µm thick slices of cat lens (~0.015-0.021), but all at very low scanning speeds (0.7 to 1 µm/s).

Figure 4C:
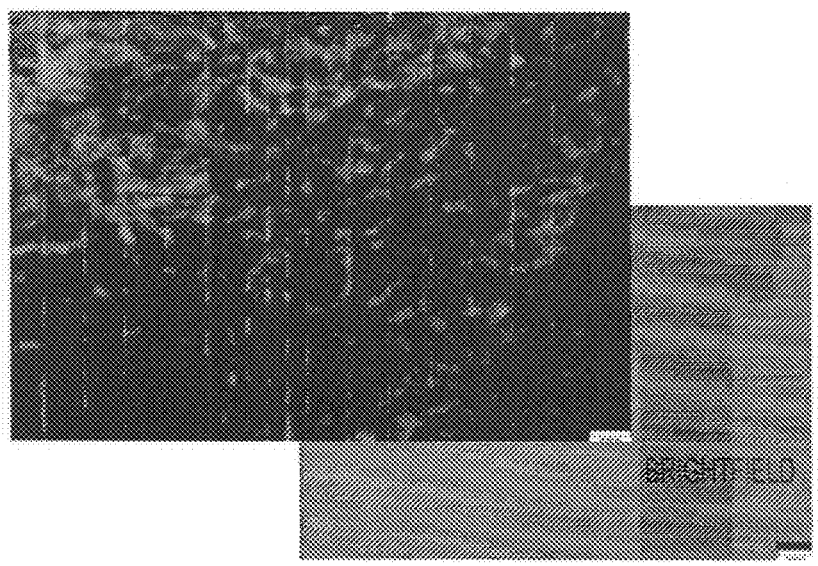
FIGS. 4C-4F show micromachining results in a cornea and a lens with Na-Fluorescein doping.
Figure 4D:
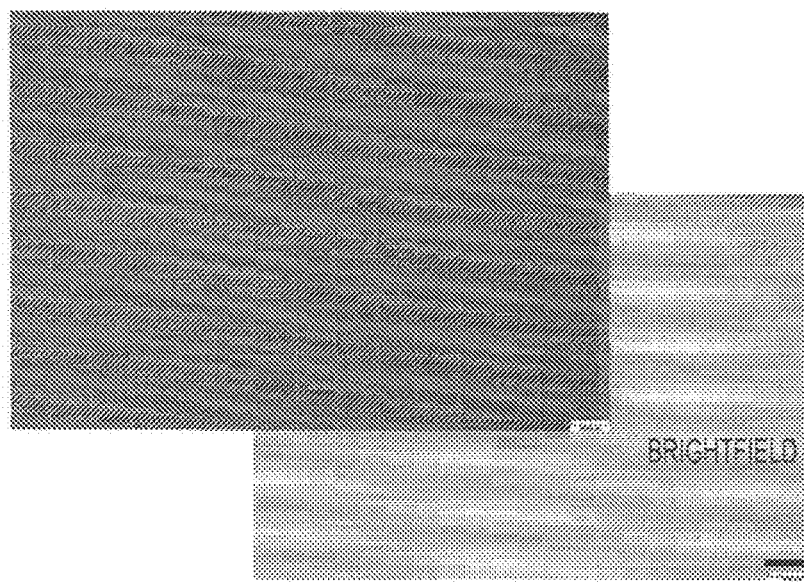
Figure 4E:
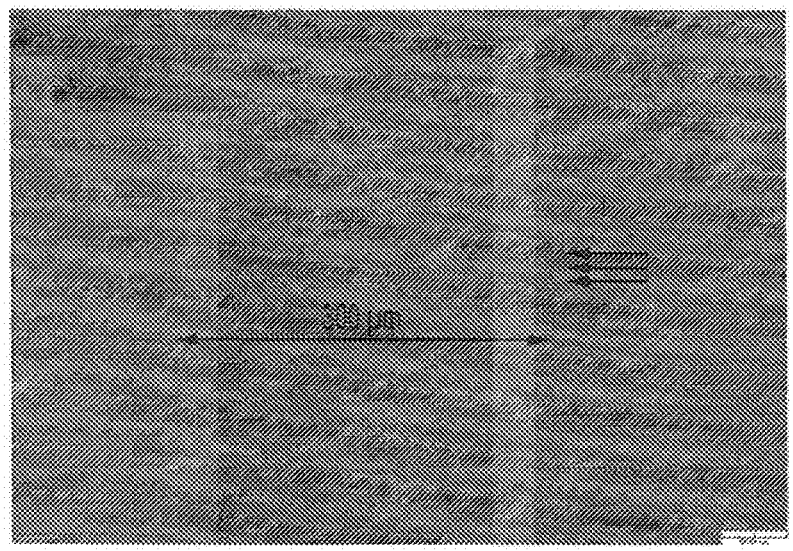
Figure 4F:
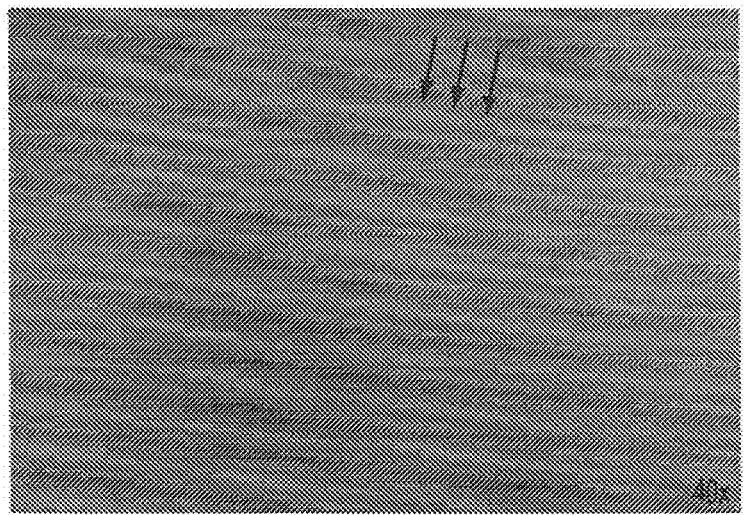

A reason why writing speeds were so slow in the cornea and the lens in early tests is that these clear biological tissues possess natively low two-photon absorption (TPA) properties. Thus, it was hypothesized that if the TPA of cornea and lens could be increased through the incorporation of a two-photon absorbing chromophore, this should theoretically increase the rate and magnitude of IRIS in these tissues. Sodium Fluorescein is one such chromophore, which is already commonly used in ophthalmic (and medical) practice. It is non-toxic to the living eye and can even be injected intravenously (e.g. for retinal angiography). To test the hypothesis, lightly-fixed cornea and lens pieces were incubated in a 25% solution of Sodium Fluorescein in ethylene glycol/sucrose/PBS overnight. Both tissue types readily absorbed the chromophore and turned slightly orange. They were then rinsed and IRIS was performed as described above. In Fluorescein-treated cat corneas, scanning speeds of 1 mm/s (~1,400× faster than in non-treated corneas) were attained and used to create multiple lines that were several mm long, and whose refractive index change averaged 0.02 (up to 4× larger than in non-treated corneas). Just as in the non-fluorescein treated corneas, these features were long-lived, lasting through several months of refrigerated storage. FIG. 4C is a phase contrast image showing the refractive index change lines in a cornea doped with 25% sodium fluorescein after micromachining with a scanning speed of 1 mm/s, an average power of 120 mW, a depth below the surface of 120 µm, and a laser wavelength of 800 nm. FIG. 4D is a phase contrast image showing the refractive index change lines in an intraocular lens doped with 25% sodium fluorescein after micromachining with a scanning speed of 1 mm/s, an average power of 100 mW, a depth below the surface of 120 µm, and a laser wavelength of 800 nm. FIG. 4E is a phase contrast image showing a 300 µm wide band micromachined in a doped cat cornea 100 µm below the surface using 20 fs laser pulses, a scanning speed of 1 mm/s, an average power of 120 mW, and a laser wavelength of 800 nm. The image in FIG. 4E was taken right after micromachining. FIG. 4F is an image taken after the fluoroscein has been rinsed off. In addition to sodium fluoroscein, other absorbing chromophores may be similarly used, such as coumarin, riboflavin, or acetaminophen.

Femtosecond laser treatment is performed under surgical or topical anesthesia as previously described for conventional laser refractive surgery (Bithren, Yoon, Kenner, MacRae & Huxlin, 2007b, Nagy et al., 2007). The subjects are placed into a specially designed head-mount, which will hold them in a supine position, with the eyes facing directly upwards. A drop of 0.5% Proparacaine Hydrochloride (or other ophthalmic anesthetic agent) will be placed in the eye to be treated. One to two drops of 20% NaFluorescein in a 10% solution of dimethyl sulfoxide (DMSO) in Celluvisc will also be administered to each eye to be treated in order to increase the two-photon absorption rate of the cornea. Pilot experiments show that 10 minutes is sufficient to allow penetration of the fluorescein chromophore through the entire thickness of the cornea (see FIGS. 5A and 5B). Lower and higher concentrations of Na Fluorescein also work, but the amount of time required for penetration increases at lower concentrations. The corneal surface can then be kept moist with the application of saline or ophthalmic moistening agents. Once corneal reflexes have disappeared, the subject can then undergo IRIS treatment over a circular (or otherwise shaped) area 6 mm (or other dimensions, as required) in diameter, in the center (or other location) of its cornea, at a depth of 100 µm (or other depths) below or within the surface epithelium. Other positional parameters can be used if needed. The eye can be kept immobile during the laser treatment by a fixation target or by conjunctival structures, which will be removed at the end of the operation. An infrared CCD camera is used to monitor the micromachining process and the generation of visible plasma luminescence in real-time. The treatment should take about 5-10 minutes per eye, after which the subject will be recovered as clinically prescribed.

FIGS. 5A and 5B: Slit lamp imaging of the cornea of an anesthetized cat with Fluorescein filter, demonstrating penetration of NaFluorescein into the stroma within 10 minutes of its topical application to the eye. 5A. Slit lamp image taken immediately after application of 25% NaFluorescein to the ocular surface. Only the surface epithelium (arrowed) stained. The rest of the corneal depth (approx. to the dotted white line) is completely black. 5B. Slit lamp image of the cornea in FIG. 5A, taken 10 minutes later. The epithelium (arrowed) is still labeled, but now Fluorescein can be seen deeper in the stroma, almost to the endothelium (~dotted line).

A similar protocol, with the major difference being that the Na Fluorescein solution might have to be injected into the anterior chamber of the eye, could be used to enhance TPA in the living lens. IRIS could be performed in the lens by simply using a longer-working-distance focusing objective to focus the femtosecond laser beam into the lens in situ.

In order to assess whether chemical fixation of the cornea with paraformaldehyde was critical to attaining IRIS in the cornea, IRIS on a non-fixed (fresh), post-mortem cat cornea immediately after enucleation was performed. Several small gratings were inscribed one above the other in the corneal stroma and they were imaging with optical coherence tomography (OCT). Stacking several gratings together assured that the OCT, with a resolution of ~10 µm, could actually resolve these features, given that individual IRIS lines were only 1-3 µm thick. The results of this experiment was reported at an ARVO meeting (Huxlin et al., 2008) and some pictures are provided in FIGS. 6A-6C. Thus, while fixation may influence the magnitude of RI change attained, IRIS does not actually require it.

FIGS. 6A-6C: IRIS in the unfixed cat cornea. 6A. Front view of the cat eye just prior to excision of the globe. 6B. Schematic diagram of the view of the eye shown in FIG. 6A, illustrating the different visible features (cat iris and pupil) as well as the location of the femtosecond treatment (magnified below in DIC mode) at the bottom of the cornea. The long, black, vertical line through the rectangular IRIS pattern indicates the imaging plane used for optical coherence tomography (OCT). 6C. OCT image of the corneal layers collected through the rectangular IRIS grating (in the plane of the thin black vertical line in FIG. 6B). The IRIS pattern is visible as a thin, horizontal line of increased reflectivity (inside the white rectangle) within the corneal stroma, about 200 µm below the epithelial (epi) surface.

IRIS does not change the Raman spectrum of hydrogels—changes in refractive index, not material composition or chemistry. Balafilcon A hydrogel polymer (Bausch & Lomb, USA) was used for this experiment, whose goal was to gain insight into the mechanisms by which femtosecond micromachining achieved its refractive index change in hydrated, optically clear but non-biological materials. The chemical components of the hydrogel used (Balafilicon A) included tris-(trimethylsiloxy)-silyl propylvinyl carbamate (TPVC), N-vinyl pyrrolidone (NVP) and other types of silicones (Karlgard, Sarkar, Jones, Moresoli & Leung, 2004). Balafilicon A contains 36% water by weight and has an average refractive index of 1.4220 (Ding et al., 2006). The cutoff wavelength of its transmission spectra are within the range of 300 to 350 nm, and its transmissivity at 800 nm is ~83% (Ding et al., 2006). A Kerr-lens mode-locked Ti:Sapphire femtosecond laser oscillator (K-M Labs), generating pulses of 300 mW average power, 27 fs pulsewidth and 93 MHz repetition rate at 800 nm was focused into the hydrogels using a 60×0.70NA Olympus LUCPlanFLN long-working-distance objective. Throughout the whole experimental process, the hydrogel samples were mounted in a Borate Buffered Saline (BBS) solution between two cover glass slides and maintained their water-content. A 3D scanning platform formed by three Newport VP-25XA linear servo stages with 100 nm resolution was employed to move the hydrogel samples transversely to the direction of the laser beam. Smooth lines 40 µm long were inscribed just below the hydrogel surface using 1.3 nJ pulse-energies, which were below the optical breakdown threshold of the material. These low pulse-energies created a 0.06 refractive index change along the lines. Using the same knife edge method reported previously (Ding et al., 2006), a laser focal diameter of about 2.5 µm was measured. This focal diameter gave rise to laser-irradiated lines about 1 µm wide and 3 µm deep.

Figure 7A:
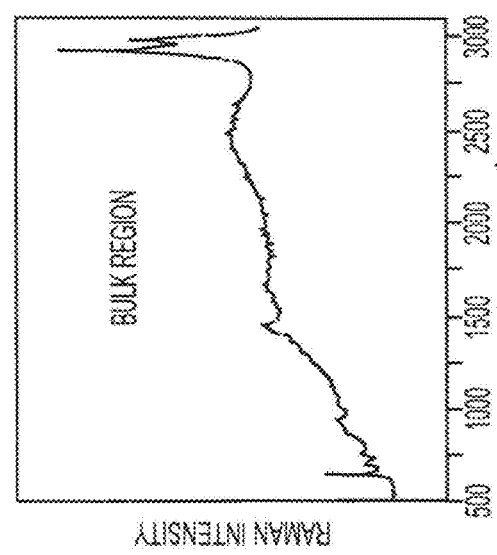
FIGS. 7A-7D show the effects on the Raman spectrum.
Figure 7B:
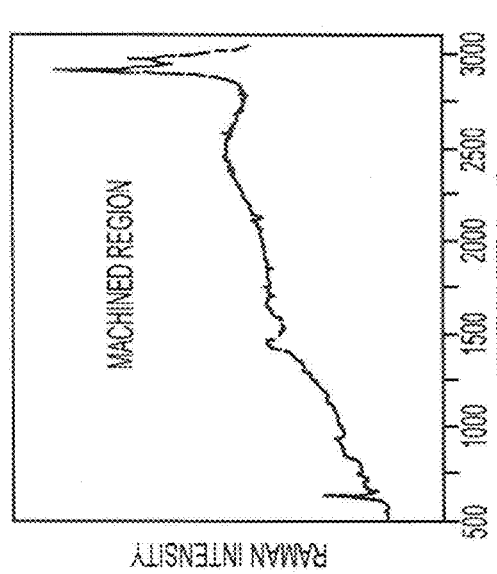
Figure 7C:
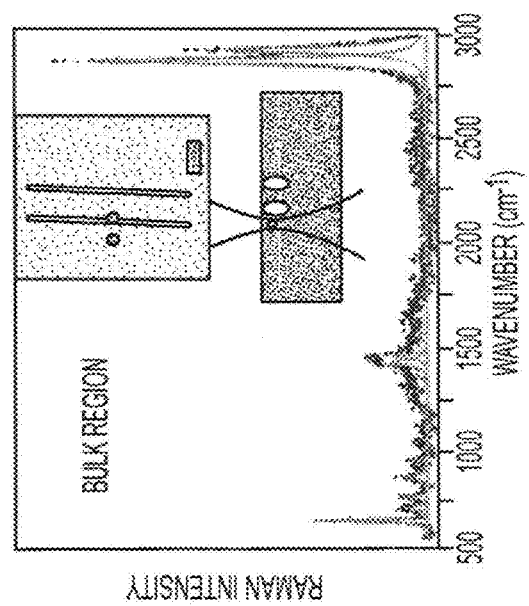

In order to check for structural modifications in the machined region, several Raman spectra were measured in 400 nm steps both within and next to the micromachined lines using a 3 mW, 632.8 nm HeNe laser. In both spectra, several Raman peaks were detected over the broad background fluorescence (FIGS. 7A, B). Differences in the background fluorescence of the two spectra were first measured since some of the defects generated by MHz femtosecond laser pulses are known to increase fluorescence intensity in fused silica (Reichman, Krol, Shah, Yoshino, Arai, Eaton & Herman, 2006). Here however, no significant changes in background fluorescence were detected. The Raman signal was then calculated by subtracting the background fluorescence from the original spectrum (FIGS. 7C, D). The Raman peaks could be assigned to different material bonds activities (see FIG. 7D), but most importantly, the Raman spectra obtained from the machined region were almost identical to the Raman spectra obtained from the untreated regions of hydrogel, suggesting that the micromachining process did not induce significant structural and chemical changes in the hydrogel polymer.

Figure 7D:
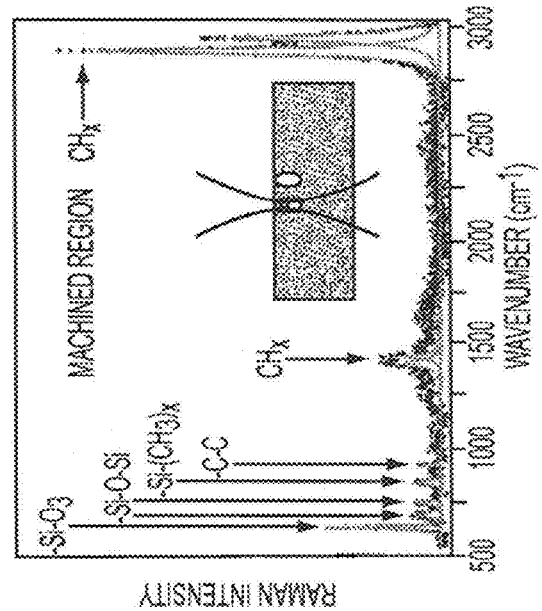

FIG. 7A. Raman spectrum of an untreated (bulk) region of Balafilcon A hydrogel in BBS solution, showing significant background fluorescence over which spectral peaks are superimposed. FIG. 7B. Raman spectrum of one of the fs laser-modified lines inside a Balafilcon A hydrogel piece (see insets in FIG. 7C). FIG. 7C. Raman spectrum of the untreated bulk region of the Balafilcon A hydrogel imaged in FIG. 7A, with background correction. The lower insert illustrates the plane of Raman imaging in a schematic cross section of the modified hydrogel piece photographed above it. The photograph inset is a DIC image of the two micromachined lines. Scale bar=10 µm. FIG. 7D. Raman spectrum of one of the micromachined lines with background correction, showing peaks that are identical in location and magnitude to the adjacent, bulk region imaged in FIG. 7C.

Figure 8A:
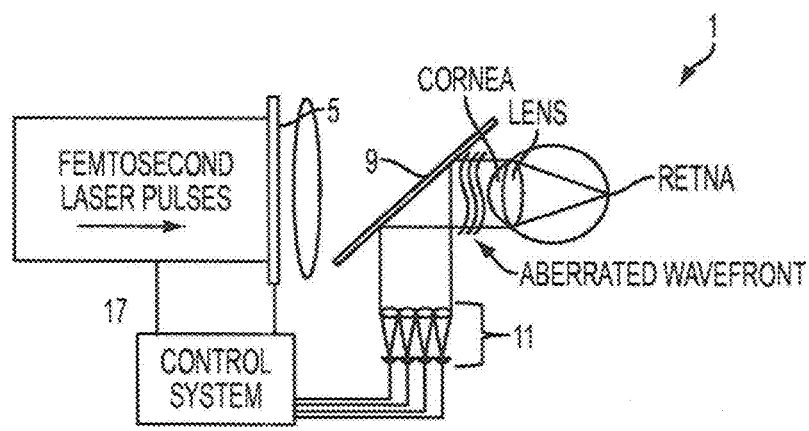
FIGS. 8A-8C show a device on which embodiments can be implemented.
Figure 8B:
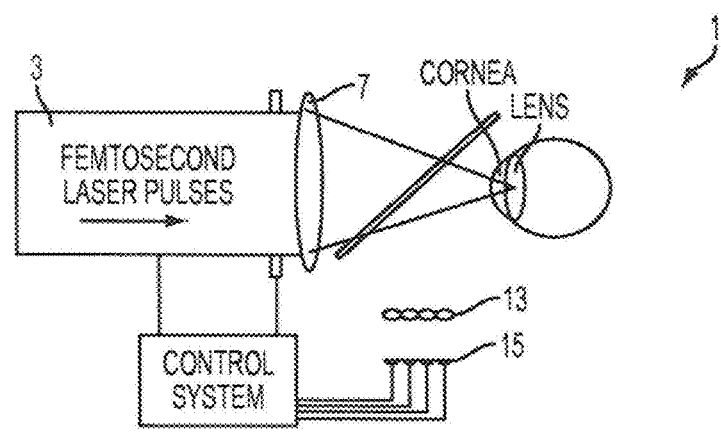
Figure 8C:
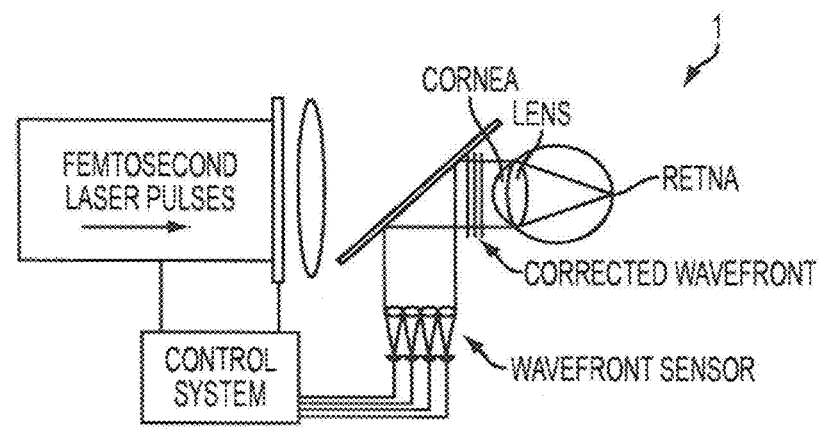

FIGS. 8A-8C show a schematic diagram of a device 1 used to carry out the preferred embodiment or another embodiment. The device 1 includes a laser 3 for emitting femtosecond laser pulses, a shutter 5, a focusing lens 7, a dichroic mirror 9, a wavefront sensor 11 having a lenslet array 13 and a detector array 15, and a control system 17 for controlling the operations described herein.

As illustrated in FIGS. 8A-8C, the process would include the following steps: (1) using a wavefront sensor to detect and measure the lower and higher order aberrations along the optical path of a given eye, (2) calculating the topography and magnitude of refractive index changes required to achieve the necessary aberration correction, (3) focusing the femtosecond laser pulses either into the cornea or intraocular lens in order to carry out the micromachining necessary to induce the required refractive index change. Once the micromachining is complete, the wavefront sensor would be used once again to check the correction of the ocular wavefront. Since the resolution of the femtosecond laser micromachining is about 1 µm, this noninvasive method could be used as a complement or an alternative method for current customized wavefront correction methods.

In FIG. 8A, the shutter 5 is closed for detection of wavefront aberration from the optical path through the wavefront sensor 11, using aberrated light A reflected from the retina R of the eye E. In FIG. 8B, the shutter is open, and light pulses P from the femtosecond laser 3 are used to correct the aberration by locally changing the index in the cornea C or the lens L. In FIG. 8C, after femtosecond laser micromachining, the wavefront correction is verified once again using the wavefront sensor.

In particular embodiments, refractive corrector elements may be formed by irradiating an optical, polymeric material, or by direct writing into the human cornea, with very short laser pulses of light as described in U.S. Publication Nos. 2008/0001320, 2009/0287306, 2012/0310340 and 2012/0310223 incorporated by reference herein, where such short laser pulses are of sufficient energy such that the intensity of light within the focal volume will cause a nonlinear absorption of photons (typically multi-photon absorption) and lead to a change in the refractive index of the material within the focal volume, while the material just outside of the focal volume will be minimally affected by the laser light. The femtosecond laser pulse sequence pertaining to an illustrative embodiment, e.g., operates at a high repetition-rate, e.g., 10 MHz, 50 MHz, 80 MHz or higher, and consequently the thermal diffusion time (>0.1 µs) is much longer than the time interval between adjacent laser pulses (~11 ns). Under such conditions, absorbed laser energy can accumulate within the focal volume and increase the local temperature. This thermal mechanism likely plays a role in the formation of laser-induced refractive structures in optical, polymeric materials. Moreover, the presence of water in the polymeric material is believed to advantageously influence the formation of the refractive structures. As such, optical hydrogel polymers provide greater processing flexibility in the formation of the refractive structures as compared to zero or low water content optical polymers, e.g., the hydrophobic acrylates or low-water (1% to 5% water content) acrylate materials. The irradiated regions exhibit little or no scattering loss, which means that the resulting refractive structures that form in the focal volume are not clearly visible under appropriate magnification without phase contrast enhancement. In other words, the refractive structures are virtually transparent to the human eye without some form of image enhancement. The change in refractive index in the irradiated regions may be either positive or negative, depending on the combination of materials and wavelengths used. An optical material is a polymeric material that permits the transmissions of at least 80% of visible light through the material, that is, an optical material does not appreciably scatter or block visible light.

According to specific embodiments, refractive correctors may be formed by providing an optical, polymeric lens material having an anterior surface and posterior surface and an optical axis intersecting the surfaces; and forming at least one laser-modified layer disposed between the anterior surface and the posterior surface with light pulses from a laser by scanning the light pulses along regions of the optical, polymeric material to cause changes in the refractive index of the polymeric lens material. In such embodiment, the at least one laser-modified layer forms at least part of a desired refractive element formed to compensate for at least one vision problem as further described herein.

According to further embodiments, a refractive property of ocular tissue in an eye is modified by forming at least one optically-modified layer in at least one of the corneal stroma and the crystalline lens ocular tissue in an eye by scanning light pulses from a laser focused in the corneal stroma or crystalline lens ocular tissue along regions of the corneal stroma or crystalline lens ocular tissue to cause changes in the refractive index within the ocular tissue to form a modified corneal stroma or crystalline lens. In such embodiment, the at least one optically-modified layer forms at least part of a desired refractive element formed to compensate for at least one vision problem as further described herein.

Femtosecond laser pulse writing methods may be more advantageously carried out if an optical polymeric material, such as, e.g., an optical hydrogel material, includes a photosensitizer, as more particularly taught in U.S. Publication Nos. 2009/0287306 and 2012/0310340 incorporated by reference herein. The presence of the photosensitizer permits one to set a scan rate to a value that is at least fifty times greater, or at least 100 times greater, than a scan rate without a photosensitizer present in the material, and yet provide similar refractive structures in terms of the observed change in refractive index of the material in the focal volume. Alternatively, the photosensitizer in the polymeric material permits one to set an average laser power to a value that is at least two times less, more particularly up to four times less, than an average laser power without a photosensitizer in the material, yet provide similar refractive structures. A photosensitizer having a chromophore with a relatively large multi-photon absorption cross section is believed to capture the light radiation (photons) with greater efficiency and then transfer that energy to the optical polymeric material within the focal volume. The transferred energy leads to the formation of the refractive structures and the observed change in the refractive index of the material in the focal volume. Some examples of such photosensitizers include sodium fluoroscein, coumarin, riboflavin or various UV-blockers, such as UVAM or methine dyes.

A 60×0.70NA Olympus LUCPlanFLN long-working-distance microscope objective with variable spherical aberration compensation may be employed to laser-write refractive segments. As indicated by the following equation $$\Delta T(r, z, t = 0) = \frac{\beta \tau_P [I(0, 0)]^2 \exp\left[-4\left(\frac{r^2}{a^2} + \frac{z^2}{b^2}\right)\right]}{c_p \rho}$$

the localized instantaneous temperature depends on both the pulse intensity and the magnitude of the two-photon absorption (TPA) coefficient. In order to produce an optical modification of a material that is of purely refractive character, i.e., non-absorbing or scattering, it is important to avoid optical damage, i.e., observed burning (scorching) or carbonization of the polymeric material. Such material or optical damage can be caused by excitation intensities exceeding a critical free-electron density. For hydrogel polymers containing a fair amount of water, the optical breakdown threshold is much lower than that in silica glasses. This breakdown threshold limits the pulse energy (in many cases to approximately 0.1 nJ to 20 nJ) that the hydrogel polymers can tolerate, and yet provide the observed changes in the refractive index within the focal volume.

Another way to increase energy absorption at a given intensity level is to increase the nonlinear absorption coefficient $\beta$ by doping the optical, polymeric material with a particular chromophore and tuning the short pulse laser near a two-photon transition of the chromophore. In this regard, optical, hydrogel materials doped with a non-polymerizable photosensitizer or a polymerizable photosensitizer have been prepared. The photosensitizer may include a chromophore having a two-photon, absorption cross-section of at least 10 GM between a laser wavelength range of 750 nm to 1100 nm. In the former case of a non-polymerizable photosensitizer, solutions containing a photosensitizer may be prepared and the optical, hydrogel polymeric materials may be allowed to come in contact with such solutions to allow up-take of the photosensitizer into the polymeric matrix of the polymer. In the later case of a polymerizable photosensitizer, monomers containing a chromophore, e.g., a fluorescein-based monomer, may be used in the monomer mixture used to form the optical, polymeric material such that the chromophore becomes part of the polymeric matrix. Further, one could easily use a solution containing a non-polymerizable photosensitizer to dope an optical, polymeric material that had been prepared with a polymerizable photosensitizer. Also, it is to be understood that the chromophoric entities could be the same or different in each respective photosensitizer.

The concentration of a polymerizable, monomeric photosensitizer having a two-photon, chromophore in an optical material, preferably an optical, hydrogel material, can be as low as 0.05 wt. % and as high as 10 wt. %. Exemplary concentration ranges of polymerizable monomer having a two-photon, chromophore in an optical, hydrogel material is from 0.1 wt. % to 6 wt. %, 0.1 wt. % to 4 wt. %, and 0.2 wt. % to 3 wt. %. In various aspects, the concentration range of polymerizable monomer photosensitizer having a two-photon, chromophore in an optical, hydrogel material is from 0.4 wt. % to 2.5 wt. %.

Due to the high repetition rate pulse sequence used in the irradiation process, the accumulated focal temperature increase can be much larger than the temperature increase induced by a single laser pulse. The accumulated temperature increases until the absorbed power and the dissipated power are in dynamic balance. For hydrogel polymers, thermal-induced additional crosslinking within the polymer network can produce a change in the refractive index as the local temperature exceeds a transition temperature. The refractive index change may be positive or negative. If the temperature increase exceeds a second threshold, a somewhat higher temperature than the transition temperature, the polymer is pyrolytically degraded and carbonized residue and water bubbles are observed. In other words, the material exhibits visible optical damage (scorching). Each of the following experimental parameters such as laser repetition rate, laser wavelength and pulse energy, TPA coefficient, and water concentration of the materials should be considered so that a desired change in the refractive index can be induced in the hydrogel polymers without optical damage.

The pulse energy and the average power of the laser, and the rate at which the irradiated regions are scanned, will in-part depend on the type of polymeric material that is being irradiated, how much of a change in refractive index is desired and the type of refractive structures one wants to create within the material. The selected pulse energy will also depend upon the scan rate and the average power of the laser at which the refractive structures are written into the polymer material. Typically, greater pulse energies will be needed for greater scan rates and lower laser power. For example, some materials will call for a pulse energy from 0.05 nJ to 100 nJ or from 0.2 nJ to 10 nJ.

Within the stated pulse energies above, the optical, hydrogel polymeric material may be irradiated at a scan rate of at least 0.1 mm/s, or at least 1 mm/s or at least 10 mm/s, and can range, e.g., up to 50 mm/s or even higher. For example, scan speeds of 100 mm/s, 200 mm/s, 400 mm/s and up to 700 mm/s and even higher and all speeds in between are valuable and many have been demonstrated and are effective to reduce the scan time. Apparatus which may be employed in the present disclosure and which is capable of obtaining such high scanning speeds is described, e.g., in WO 2015/006274, the disclosure of which is incorporated by reference herein in its entirety, and may include, for example, scan stages, spinning polygonal mirrors, galvo mirrors, circular stages, etc. and any combinations thereof.

Within the stated pulse energies and scan rates above, the average laser power used in the irradiation process may be, e.g., from 10 mW to 3 watts or more, or 10 mW to 800 mW, or from 40 mW to 400 mW.

In one example, the average pulse energy may be from 0.2 nJ to 10 nJ and the average laser power may be from 40 mW to 220 mW. The laser also may operate within a wavelength of 500 nm to 1200 nm, or 650 nm to 950 nm or in the 1030 to 1050 nm range. Within the stated laser operating powers, the optical, hydrogel polymeric material may be irradiated at a scan rate, e.g., of greater than 4 mm/s, and preferably at greater than 10 mm/s. In further examples using average laser powers greater than 200 mW, the scan rates may range above 10 mm/s, even as high as 500 mm/s or higher.

A photosensitizer will include a chromophore in which there is little or no intrinsic linear absorption in the spectral range of 600-1100 nm. The photosensitizer is present in the optical, hydrogel polymeric material to enhance the photo-efficiency of the two-photon absorption required for the formation of the described refractive structures. Photosensitizers of particular interest include, but are not limited to, the following compounds. The compounds below are merely exemplary. Additional examples may include UVAM, other UV dyes used in contacts or IOLs, methine dyes, riboflavin, acetaminophen, and so forth.

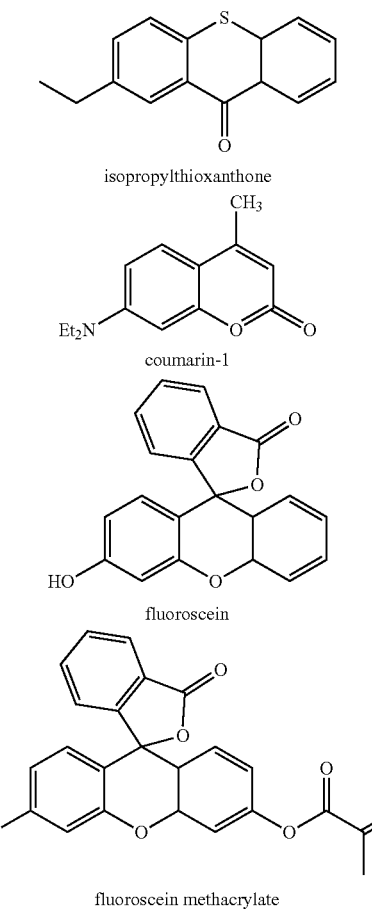

isopropylthioxanthone coumarin-1 fluoroscein fluoroscein methacrylate

As described in U.S. Publication Nos. 2009/0287306 and 2012/0310340 in greater detail in the Example sections, a commercial IOL material, Akreos®, presently marketed by Bausch & Lomb, was subjected to laser irradiation according to the processes described therein. An Akreos® IOL is a HEMA-based, hydrogel material with 26% to 28% water content. The micromachining process was used to imprint refractive structures in an Akreos® IOL without photosensitizer and an Akreos® IOL doped with a solution containing 17 wt. % coumarin-1. The irradiation experiments were conducted with both dry and hydrated materials. The refractive structures formed only in the hydrated materials. In brief, the magnitude of the measured change in refractive index was at least ten times greater in the Akreos® IOL doped with the coumarin solution at a given scan rate and an average laser power than the Akreos® IOL without the coumarin.

In another illustrative aspect described in U.S. Publication Nos. 2009/0287306 and 2012/0310340, a balafilcon A silicone hydrogel was prepared by adding fluorescein monomer (0.17% by weight) as a polymerizable photosensitizer to the polymer monomer mixture. The balafilcon A doped with fluorescein was then subjected to laser radiation according to the processes described therein. Again, the described irradiation process was used to imprint refractive structures in the silicone hydrogel without photosensitizer and the silicone hydrogel doped with 0.17 wt. % fluorescein monomer. Again, experiments were conducted with both dry and hydrated materials, and again, the refractive structures formed only in the hydrated materials. In brief, the magnitude of the measured change in refractive index was at least ten times greater in the balafilcon A silicone hydrogel doped with 0.17 wt. % fluorescein monomer at an average laser power of 60 mW than balafilcon A without the photosensitizer. This 10-fold difference in change in refractive index was observed even with a 10-fold increase in scan rate in the photosensitized material; i.e., 0.5 mm/s in the undoped material and 5.0 mm/s in the photosensitized material.

The laser may generate light with a wavelength in the range from violet to near-infrared. In various aspects, the wavelength of the laser may be in the range from 400 nm to 1500 nm, from 400 nm to 1200 nm, or from 650 nm to 950 nm.

In an exemplary aspect, the laser may be a pumped Ti:sapphire laser with an average power of 10 mW to 1000 mW or higher. Such a laser system will generate light with a wavelength of approximately 800 nm. In another exemplary aspect, an amplified fiber laser that can generate light with a wavelength from 1000 nm to 1600 nm may be used.

The laser may have a peak intensity at focus of greater than $10^{13}$ W/cm$^2$. At times, it may be advantageous to provide a laser with a peak intensity at focus of greater than $10^{14}$ W/cm$^2$, or greater than $10^{15}$ W/cm$^2$.

The ability to form refractive structures in optical polymeric materials provides an important opportunity to an ophthalmic surgeon or practitioner to modify the refractive index of an optical device, e.g., an intraocular lens or corneal inlay, following implantation of the device into an eye of a patient. The method allows the surgeon to correct aberrations as a result of the surgery. The method also allows the surgeon to adjust the refractive properties of the lens or inlay by adjusting the refractive index in the irradiated regions based on the vision correction required of each patient. For example, starting from a lens of selected power (will vary according to the ocular requirements of the patient), the surgeon can further adjust the refractive properties of the lens to correct a patient's vision based upon the individual needs of the patient. In essence, an intraocular lens would essentially function like a contact lens or glasses to individually correct for the refractive error of a patient's eye. Moreover, because the implanted lens can be adjusted by adjusting the refractive index of select regions of the lens, post-operative refractive errors resulting from pre-operative measurement errors, variable lens positioning during implantation, and wound healing (aberrations) can be corrected or fine tuned in-situ.

The irradiated portions of the optical, hydrogel polymeric material may exhibit a positive change in refractive index of about 0.01 or more. In one embodiment, the refractive index of the region will increase by about 0.03 or more. As disclosed in U.S. Publication Nos. 2009/0287306 and 2012/0310340, a positive change in refractive index in a hydrated, Akreos® IOL material of about 0.06 has been measured. In some cases the refractive index change will be negative (i.e. reducing the refractive index relative to the native material index before radiation). The magnitude of the negative change has been shown to be about 0.01 or greater (i.e. −0.01 to −0.06 or even more). As disclosed for example in Femtosecond Laser Writing of freeform gradient index microlenses in hydrogel-based contact lenses, Gandara-Montano et al., in Optical Materials Express, vol. 5, no. 10, which is hereby incorporated by reference in its entirety, a negative change in refractive index in a Johnson & Johnson Acuvue 2 contact lens material of about −0.03 or more has been measured.

In an exemplary aspect, the irradiated regions of an optical, polymeric material can be defined by two- or three-dimensional structures providing the desired wavefront cross-section profile. The two- or three-dimensional structures can comprise an array of discrete cylinders, a series of lines, or a combination of an array of cylinders and a series of lines. Moreover, the two- or three-dimensional structures can comprise area or volume filled structures, respectively. These area or volume filled structures can be formed by continuously scanning the laser at a constant or varying scan rate over a selected region of the polymeric material.

In one aspect, the refractive structures may be formed proximate to the top anterior surface of an intraocular lens. For example, a positive or negative lens element (three-dimensional) is formed within a 300 μm volume, or within a 100 μm volume, from the anterior surface of the lens. The term "anterior surface" is the surface of the lens that faces the anterior chamber of a human eye.

Figure 9:
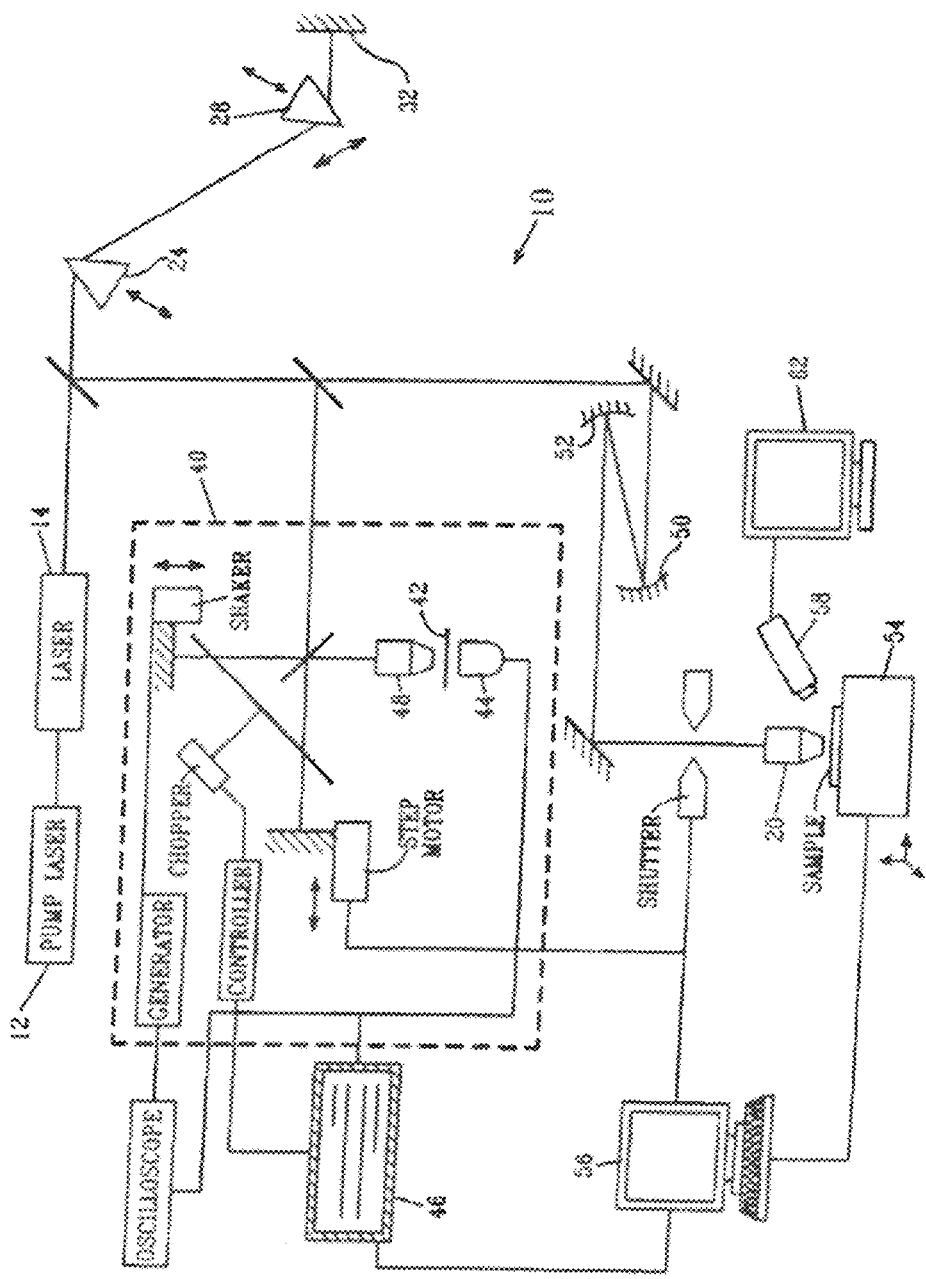
FIG. 9 shows an embodiment of a laser system that may be used in the preset disclosure.

A non-limiting embodiment of a laser system 10 which may be used for irradiating an optical, polymeric material with a laser to modify the refractive index of the material in select regions to form a refractive corrector having a wavefront cross-section phase profile as described herein is illustrated in FIG. 9. A laser source comprises a Kerr-lens mode-locked Ti:Sapphire laser 12 (Kapteyn-Murnane Labs, Boulder, Colo.) pumped by 4 W of a frequency-doubled Nd:YVO4 laser 14. The laser generates pulses of 300 mW average power, 30 fs pulse width, and 93 MHz repetition rate at wavelength of 800 nm. Because there is a reflective power loss from the mirrors and prisms in the optical path, and in particular from the power loss of the objective 20, the measured average laser power at the objective focus on the material is about 120 mW, which indicates the pulse energy for the femtosecond laser is about 1.3 nJ. More recent examples have achieved greater than 200 mW average laser power at the objective focus, and in some cases greater than 500 mW.

Due to the limited laser pulse energy at the objective focus, the pulse width must be preserved so that the pulse peak power is strong enough to exceed the nonlinear absorption threshold of the materials. Because a large amount of glass inside the focusing objective significantly increases the pulse width due to the positive dispersion inside of the glass, an extra-cavity compensation scheme is used to provide the negative dispersion that compensates for the positive dispersion introduced by the focusing objective. Two SF10 prisms 24 and 28 and one ending mirror 32 form a two-pass, one-prism-pair configuration. In a particular instance, a 37.5 cm separation distance between the prisms is used to compensate for the positive dispersion of the microscope objective and other optics within the optical path.

A collinear autocorrelator 40 using third-order harmonic generation is used to measure the pulse width at the objective focus. Both 2nd and 3rd harmonic generation have been used in autocorrelation measurements for low NA or high NA objectives. Third-order surface harmonic generation (THG) autocorrelation may be used to characterize the pulse width at the focus of the high-numerical aperture (NA)

objectives because of its simplicity, high signal to noise ratio, and lack of material dispersion that second harmonic generation (SHG) crystals usually introduce. The THG signal is generated at the interface of air and an ordinary cover slip 42 (Corning No. 0211 Zinc Titania glass), and measured with a photomultiplier 44 and a lock-in amplifier 46. After using a set of different high-numerical-aperture objectives and carefully adjusting the separation distance between the two prisms and the amount of glass inserted, a transform-limited 27 fs duration pulse is used, which is focused by a 60×0.70NA Olympus LUCPlanFLN long-working-distance objective 48.

Because the laser beam will spatially diverge after it comes out of the laser, a concave mirror pair 50 and 52 is added into the optical path in order to adjust the dimension of the laser beam so that the laser beam can optimally fill the objective aperture. A 3D 100 nm resolution DC servo motor stage 54 (Newport VP-25XA linear stage) and a 2D 0.7 nm resolution piezo nanopositioning stage (PI P-622.2CD piezo stage) are controlled and programmed by a computer 56 as a scanning platform to support and locate the samples. The servo stages have a DC servo-motor so they can move smoothly between adjacent steps. An optical shutter controlled by the computer with 1 ms time resolution is installed in the system to precisely control the laser exposure time. With customized computer programs, the optical shutter could be operated with the scanning stages to micromachine different patterns in the materials using different scanning speeds at different position or depth in the optical material, and different laser exposure times. In addition, a CCD camera 58 along with a monitor 62 is used beside the objective 20 to monitor the process in real time.

The method and optical apparatus described above can be used to modify the refractive index of an intraocular lens following the surgical implantation of the intraocular lens in a human eye, or before the lens is implanted in an eye. Similarly, contact lenses and corneal inlays may also be altered before or after implant or application to an eye.

Accordingly, an embodiment described herein is directed to a method comprising identifying and measuring requisite vision correction for each patient, and once the vision correction is identified and quantified using methods well known in the art of ophthalmology, this information is processed by a computer. There are a number of commercially available diagnostic systems that are used to measure aberrations. For example, common wavefront sensors used today are based on the Schemers disk, the Shack Hartmann wavefront sensor, the Hartmann screen, and the Fizeau, and Twyman-Green interferometers. The Shack-Hartmann wavefront measurement system is known in the art and is described in-part by U.S. Pat. Nos. 5,849,006; 6,261,220; 6,271,914 and 6,270,221. Such systems operate by illuminating a retina of the eye and measuring the reflected wavefront.

Once the aberrations are identified and quantified, the computer programs determine the position and shape of the refractive structures to be written into the lens material to correct for those aberrations or to provide vision correction to the patient. These computer programs are well known to those of ordinary skill in the art. The computer then communicates with the laser-optical system and select regions of the lens are irradiated with a laser having a pulse energy from 0.05 nJ to 1000 nJ as described herein, to provide a wavefront cross-section phase profile comprising desired refractive features to provide desired vision correction in accordance with an embodiment of the present disclosure.

Optical, hydrogel polymeric materials that can be irradiated with a laser according to the methods described to form refractive correctors in accordance with various embodiments can be any optical, hydrogel polymeric material known to those of ordinary skill in the polymeric lens art, particularly those in the art familiar with optical polymeric materials used to make intraocular lenses or contact lenses. Broadly, non-limiting examples of such materials include those used in the manufacture of ophthalmic devices, such as siloxy-containing polymers, acrylic, hydrophilic or hydrophobic polymers or copolymers thereof—even though some of these hydrophobic materials may not typically be called hydrogels, they are included here and IRIS applies to such materials similarly, even if the refractive index changes may be different or less. The forming of the refractive structures is particularly suited for modifying the refractive index in select and distinct regions of a polymeric, optical silicone hydrogel, or a polymeric, optical non-silicone hydrogel.

The term "hydrogel" refers to an optical, polymeric material that can absorb greater than 10% by weight water based on the total hydrated weight. In fact, many of the optical, hydrogel polymeric materials will have a water content greater than 15% or greater than 20%. For example, many of the optical, hydrogel polymeric materials will have a water content from 15% to 60% or from 15% to 40%.

The optical, hydrogel polymeric materials are of sufficient optical clarity, and will have a relatively high refractive index of approximately 1.40 or greater, particularly 1.48 or greater. Many of these materials are also characterized by a relatively high elongation of approximately 80 percent or greater.

In one embodiment, the optical polymeric materials are prepared as a copolymer from at least three monomeric components. The first monomeric component, preferably a monomeric component with aromatic functionality, is present in the copolymer in an amount of at least 60% by weight, and its homopolymer will have a refractive index of at least 1.50, particularly at least 1.52 or at least 1.54. The second monomeric component, preferably, an alkyl(meth)acrylate, is present in the copolymer in an amount from 3% to 20% or from 3% to 10%, by weight. The first and second monomeric components together represent at least 70% by weight of the copolymer. The term "homopolymer" refers to a polymer that is derived substantially completely from the respective monomeric component. Minor amounts of catalysts, initiators, and the like can be included, as is conventionally the case, in order to facilitate the formation of the homopolymer.

Particularly useful first monomeric components include styrene, vinyl carbazole, vinyl naphthalene, benzyl(meth)acrylate, phenyl(meth)acrylate, naphthyl(meth)acrylate, 2-phenoxyethyl(meth)acrylate, 2,3-dibromopropyl-(meth)acrylate and any one mixture thereof. Particularly useful second monomeric components include n-butyl(meth)acrylate, n-hexyl(meth)acrylate, 2-ethylhexyl-(meth)acrylate, 2-ethoxyethyl(meth)acrylate, 2,3-dibromopropyl(meth)acrylate, 1,1-dihydroperfluorobutyl(meth)acrylate and any one mixture thereof.

The third monomeric component is a hydrophilic monomeric component. The hydrophilic component is present in an amount, from 2% to 30% by weight of the copolymer. The hydrophilic component is particularly present in an amount of less than about 20% by weight of the copolymer. Copolymers that include about 10% by weight or more of a hydrophilic monomeric component tend to form hydrogels if placed in an aqueous environment. The term "hydrophilic monomeric component" refers to compounds that produce hydrogel-forming homopolymers, that is, homopolymers which become associated with at least 25% of water, based on the weight of the homopolymer, if placed in contact with an aqueous solution.

Specific examples of useful hydrophilic monomeric components include N-vinyl pyrrolidone; hydroxyalkyl (meth) acrylates such as 2-hydroxyethyl (meth)acrylate, 3-hydroxypropyl (meth)acrylate, 2-hydroxypropyl (meth)acrylate, 4-hydroxybutyl (meth)acrylate, 2,3-dihydroxypropyl (meth) acrylate and the like; acrylamide; N-alkyl acrylamides such as N-methyl acrylamide, N-ethyl acrylamide, N-propyl acrylamide, N-butyl acrylamide and the like; acrylic acid; methacrylic acid; and the like and any one mixture thereof.

In another embodiment, the optical polymeric materials are prepared as a copolymer from at least two monomeric components and a photosensitizer. The photosensitizer can be polymerizable or be entrapped within the formed polymer. The first monomeric component is a hydrophilic monomeric component. The hydrophilic component is present in an amount from 50% to 90% by weight of the copolymer. The hydrophilic component is particularly present in an amount of 60% to 85% by weight of the copolymer. The second monomeric component, preferably, an alkyl(meth) acrylate, is present in the copolymer in an amount from 5% to 20% or from 3% to 10%, by weight. The first and second monomeric components together represent at least 90% by weight of the copolymer.

The polymeric optical materials will likely include a crosslink component that can form crosslinks with at least the first or the second monomeric components. Advantageously, the crosslink component is multi-functional and can chemically react with both the first and second monomeric components. The crosslink component is often present in a minor amount relative to the amounts of the first and second monomeric components. Particularly, the crosslink component is present in a copolymer in an amount of less than about 1% by weight of the copolymer. Examples of useful crosslink components include ethylene glycol dimethacrylate, propylene glycol dimethacrylate, ethylene glycol diacrylate and the like and mixtures thereof.

In one aspect, the optical, polymeric materials can be prepared from one or more aromatic (meth)acrylate monomers having the formula:

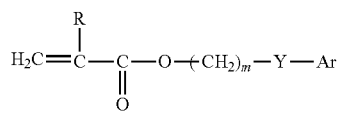

wherein: R is H or CH3; m is an integer selected from 0 to 10; Y is nothing, O, S, or NR1, wherein R1 is H, CH3, C2-C6 alkyl, iso-OC3H7, phenyl or benzyl; Ar is any aromatic ring, e.g., phenyl, which can be unsubstituted or substituted with H, CH3, C2H5, n-C3H7, iso-C3H7, OCH3, C6H11, Cl, Br, phenyl or benzyl; and a crosslinking component.

Exemplary aromatic (meth)acrylate monomers include, but are not limited to: 2 ethylphenoxy (meth)acrylate, 2-ethylthiophenyl (meth)acrylate, 2-ethylaminophenyl (meth) acrylate, phenyl-(meth)acrylate, benzyl (meth)acrylate, 2-phenylethyl (meth)acrylate, 3 phenylpropyl-(meth)acrylate, 4-phenylbutyl (meth)acrylate, 4-methylphenyl (meth) acrylate, 4 methylbenzyl (meth)acrylate, 2-2-methylphenylethyl (meth)acrylate, 2-3-methylphenylethyl (meth) acrylate, 2-4-methylphenylethyl (meth)acrylate, 2-(4-propylphenyl)ethyl (meth)acrylate, 2 (4-(1-methylethyl) phenyl)ethyl methacrylate, 2-(4-methoxyphenyl)ethyl methacrylate and the like.

Generally, if the optical, polymeric material is prepared with both an aromatic acrylate and an aromatic methacrylate as defined by the formula above, the materials will generally comprise a greater mole percent of aryl acrylate ester residues than of aryl methacrylate ester residues. It is preferred that the aryl acrylate monomers constitute from about 20 mole percent to about 60 mole percent of the polymer, while the aryl methacrylate monomers constitute from about 5 mole percent to about 20 mole percent of the polymer. Most advantageous is a polymer comprising about 30-40 mole percent 2-phenylethyl acrylate and about 10-20 mole percent 2-phenylethyl methacrylate. Hydrophilic monomer is also present in about 20-40 mole percent.

In another aspect, the optical, polymeric materials will have a fully hydrated (equilibrium) water content from 5% to 15% by weight, which also helps to minimize the degree of hazing following thermal stress as described, as well as minimize the formation of water vacuoles in-vivo. To achieve the desired water content, one may include a hydrophilic, aromatic monomer having a formula, G-D-Ar, wherein Ar is a C6-C14 aromatic group having a hydrophilic substituent, in the polymerizable compositions. D is a divalent linking group, and G is a polymerizable ethylenic site.

One particular hydrophilic aromatic monomer is represented by the formula

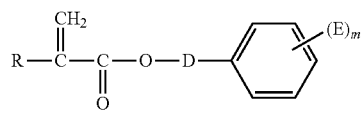

wherein R is hydrogen or CH3; D is a divalent group selected from the group consisting of straight or branched C1-C10 hydrocarbons and an alkyleneoxide (e.g., —(CH2CH2O)n-), and E is selected from the group consisting of hydrogen (if D is alkyleneoxide), carboxy, carboxamide, and monohydric and polyhydric alcohol substituents. Exemplary hydrophilic substituents include, but are not limited to, —COOH, —CH2-CH2OH, —(CHOH) 2CH2OH, —CH2-CHOH—CH2OH, poly(alkylene glycol), —C(O)O—NH2 and —C(O)—N(CH3)2.

Exemplary hydrophilic, aromatic monomers are represented by the following

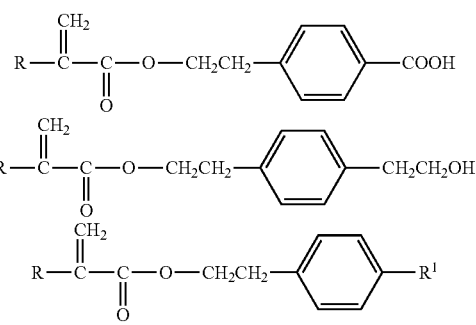

wherein R is hydrogen or CH3 and R1 is —C(O)O—NH2 or —C(O)—N(CH3)2.

In another aspect, the optical, polymeric material is prepared from a first aromatic monomeric component, which is present in 5-25% by weight, the second monomeric component is a hydrophilic monomeric component, e.g., 2-hydroxyethyl (meth)acrylate, which is present from 30 to 70% by weight; and 5 to 45% by weight of a another alkyl (meth)acrylate selected from the group consisting of methyl (meth)acrylate, ethyl (meth)acrylate, propyl (meth)acrylate, butyl (meth)acrylate, pentyl (meth)acrylate, hexyl meth) acrylate, heptyl (meth)acrylate, nonyl (meth)acrylate, stearyl meth)acrylate, octyl (meth)acrylate, decyl (meth) acrylate, lauryl (meth)acrylate, pentadecyl (meth)acrylate and 2-ethylhexyl (meth)acrylate. Among the alkyl (meth) acrylates, those containing 1 to 3 carbon atoms of alkyl group are particularly advantageous.

Exemplary aromatic monomeric components include ethylene glycol phenyl ether acrylate (EGPEA), poly(ethylene glycol phenyl ether acrylate) (polyEGPEA), phenyl methacrylate, 2-ethylphenoxy methacrylate, 2-ethylphenoxy acrylate, hexylphenoxy methacrylate, hexylphenoxy acrylate, benzyl methacrylate, 2-phenylethyl methacrylate, 4-methylphenyl methacrylate, 4-methylbenzyl methacrylate, 2-2-methyphenylethyl methacrylate, 2-3-methylphenylethyl methacrylate, 2-4-methylphenylethyl methacrylate, 2-(4-propylphenyl)ethyl methacrylate, 2-(4-(1-methylethyl) pheny)ethyl methacrylate, 2-(4-methoxyphenyl)ethylmethacrylate, 2-(4-cyclohexylpheny)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates, and including mixtures thereof. EGPEA and polyEGPEA are two of the more preferred first monomeric components.

In another aspect, the optical, polymeric material is prepared from a hydrophilic acrylic that comprises about 90% (by weight)N-vinylpyrrolidone (NVP) and about 10% (by weight) 4-t-butyl-2-hydroxycyclohexyl methacrylate. This methacrylate hydrogel can absorb about 80% (by weight) water because of the high percentage of NVP. Its refractive index when hydrated is very close to the index of water. Another hydrophilic acrylic of interest is referred to as HEMA B, which is a poly(2-hydroxyethyl methacrylate) cross-linked with about 0.9% (by weight) of ethylene glycol dimethacrylate ("EGDMA"). This HEMA-hydrogel can absorb about 37% (by weight) water.

One particular hydrophilic, acrylic material of interest is based upon a commercially available IOL sold in the market by Bausch & Lomb under the trade name Akreos®. This acrylic material comprises about 80% by weight HEMA and 20 wt % MMA.

The optical, polymeric material can also be prepared by copolymerizing a specific monomer mixture comprising perfluorooctylethyloxypropylene (meth)acrylate, 2-phenylethyl (meth)acrylate, an alkyl (meth)acrylate monomer having the following general formula,

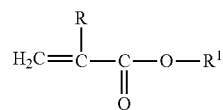

wherein R is hydrogen or methyl and R1 is a linear or branched C4-C12 alkyl group, hydrophilic monomer and a crosslinking monomer. An exemplary list of alkyl (meth) acrylate monomer include n-butyl acrylate, isobutyl acrylate, isoamyl acrylate, hexyl acrylate, 2-ethylhexyl acrylate, octyl acrylate, isooctyl acrylate, decyl acrylate, isodecyl acrylate, and the like.

The perfluorooctylethyloxypropylene (meth)acrylate is present from 5% to 20% by weight, the 2-phenylethyl (meth)acrylate is present from 20% to 40% by weight, the alkyl (meth)acrylate monomer is present from 20% to 40% by weight, the hydrophilic monomer is present from 20% to 35%, and the crosslinking agent is present from 0.5% to 2% by weight.

The optical, polymeric component will likely include a crosslinking agent. The copolymerizable crosslinking agent(s) useful in forming the copolymeric material include any terminally ethylenically unsaturated compound having more than one unsaturated group. Particularly, the crosslinking agent includes a diacrylate or a dimethacrylate. The crosslinking agent may also include compounds having at least two (meth)acrylate and/or vinyl groups. Particularly advantageous crosslinking agents include diacrylate compounds.

The optical, polymeric materials are prepared by generally conventional polymerization methods from the respective monomeric components. A polymerization mixture of the monomers in the selected amounts is prepared and a conventional thermal free-radical initiator is added. The mixture is introduced into a mold of suitable shape to form the optical material and the polymerization initiated by gentle heating. Typical thermal, free radical initiators include peroxides, such as benzophenone peroxide, peroxycarbonates, such as bis-(4-t-butylcyclohexyl) peroxydicarbonate, azonitriles, such as azobisisobytyronitrile, and the like. A particular initiator is bis-(4-t-butylcyclohexyl) peroxydicarbonate (PERK). Alternatively, the monomers can be photopolymerized by using a mold which is transparent to actinic radiation of a wavelength capable of initiating polymerization of these acrylic monomers by itself. Conventional photoinitiator compounds, e.g., a benzophenone-type photoinitiator, can also be introduced to facilitate the polymerization.

Without exclusion as to any lens materials or material modifications, e.g., the inclusion of a photosensitizer, or laser parameters described herein above, the foregoing disclosed techniques and apparatus can be used to modify the refractive properties, and thus, the dioptric power, of an optical polymeric material, typically, an optical hydrogel material, in the form of, but not limited to, an IOL, a contact lens or corneal inlay, by creating (or machining) a refractive structure with a gradient index in one, two or three dimensions of the optical material, as more fully described in U.S. Publication Nos. 2012/0310340 and 2012/0310223, incorporated by reference herein. The gradient refractive structure can be formed by continuously scanning a continuous stream of femtosecond laser pulses having a controlled focal volume in and along at least one continuous segment (scan line) in the optical material while varying the scan speed and/or the average laser power, which creates a gradient refractive index in the polymer along the segment. Accordingly, rather than creating discrete, individual, or even grouped or clustered, adjoining segments of refractive structures with a constant change in the index of refraction in the material, a gradient refractive index is created within the refractive structure, and thereby in the optical material, by continuously scanning a continuous stream of pulses. As described in greater detail in U.S. Publication No. 2012/0310340, since the refractive modification in the material arises from a multiphoton absorption process, a well-controlled focal volume corrected for spherical (and other) aberrations will produce a segment having consistent and, if desired, constant depth over the length of the scan. As further noted, when a tightly focused laser beam consisting of femtosecond pulses at high repetition rate impinges on a material that is nominally transparent at the incident laser wavelength, there is little if any effect on the material away from the focal region. In the focal region, however, the intensity can exceed one terawatt per square centimeter, and the possibility of absorbing two or more photons simultaneously can become significant. In particular, the amount of two-photon absorption can be adjusted by doping or otherwise including in the irradiated material with selected chromophores that exhibit large two-photon absorption cross-section at the proper wavelength (e.g., between 750 nm and 1100 nm), which can significantly increase the scanning speed as already described. Also, multiple segments can be written into the material in a layer using different scan speeds and/or different average laser power levels for various segments to create a gradient index profile across the layer, i.e., transverse to the scan direction. More particularly, the laser-modified GRIN layer may comprise a plurality of adjacent refractive segments having a change in the index of refraction in relation to the index of refraction of non-modified polymeric material formed with continuous streams of light pulses from a laser continuously scanned along regions of the polymeric material, wherein the plurality of adjacent refractive segments each have an independent line width and an intersegment spacing of two adjacent refractive segments is less than an average line width of the two adjacent segments so that there is overlap of the adjacent segments, and the GRIN layer is characterized by a variation in index of refraction in a direction of at least one of: (i) a transverse cross section of the adjacent refractive segments; and (ii) a lateral cross section of the refractive segments. Further, multiple, spaced gradient index (GRIN) layers can be written into the material along the z-direction (i.e., generally the light propagation direction through the material) to provide a desired refractive change in the material that corrects for some, most, or all higher order aberrations of a patient's eye. Such abilities to write continuously varying gradient index layers are particularly advantageous in forming refractive correctors having wavefront cross-section profiles in accordance with embodiments of the present disclosure. For ophthalmic applications, it is of particular interest that GRIN refractive structures are low scattering (as discussed above) and are of high optical quality.

In an illustrative aspect disclosed in U.S. Publication No. 2012/0310340, a cylindrical lens structure with a one-dimensional quadratic gradient index was written in an optical, polymeric material with three GRIN layers each 5 μm thick, spaced by 10 μm in the z-direction (i.e., a layer of non-modified optical material having a thickness of about 5 μm to 7 μm was between each two adjacent GRIN layers). The resulting cylindrical lens was designed to provide approximately 1 diopter of astigmatism uniform along the length of the device.

As further disclosed in U.S. publication No. 2012/0310223, incorporated by reference above, the femtosecond micromachining approach employed with hydrogel materials may be adapted to similarly carry out refractive correction in biological tissues by reducing the femtosecond laser pulse energies below the optical breakdown thresholds for such biological tissues, and gradient index layers may similarly be formed in such biological tissues by varying the scan rates and/or scan powers while maintaining pulse energies below such threshold energies. More particularly, refractive structures may be formed in a living eye by a method including (a) directing and focusing femtosecond laser pulses in the blue spectral region within a cornea or a lens of the living eye at an intensity high enough to change the refractive index of the cornea or lens within a focal region, but not high enough to damage the cornea or lens or to affect cornea or lens tissue outside of the focal region; and (b) scanning the laser pulses across a volume of the cornea or the lens to provide the focal region with refractive structures in the cornea or the lens. The refractive structures advantageously exhibit little or no scattering loss, which means that the structures are not clearly visible under appropriate magnification without contrast enhancement.

Binocular Corrections

Figure 14:
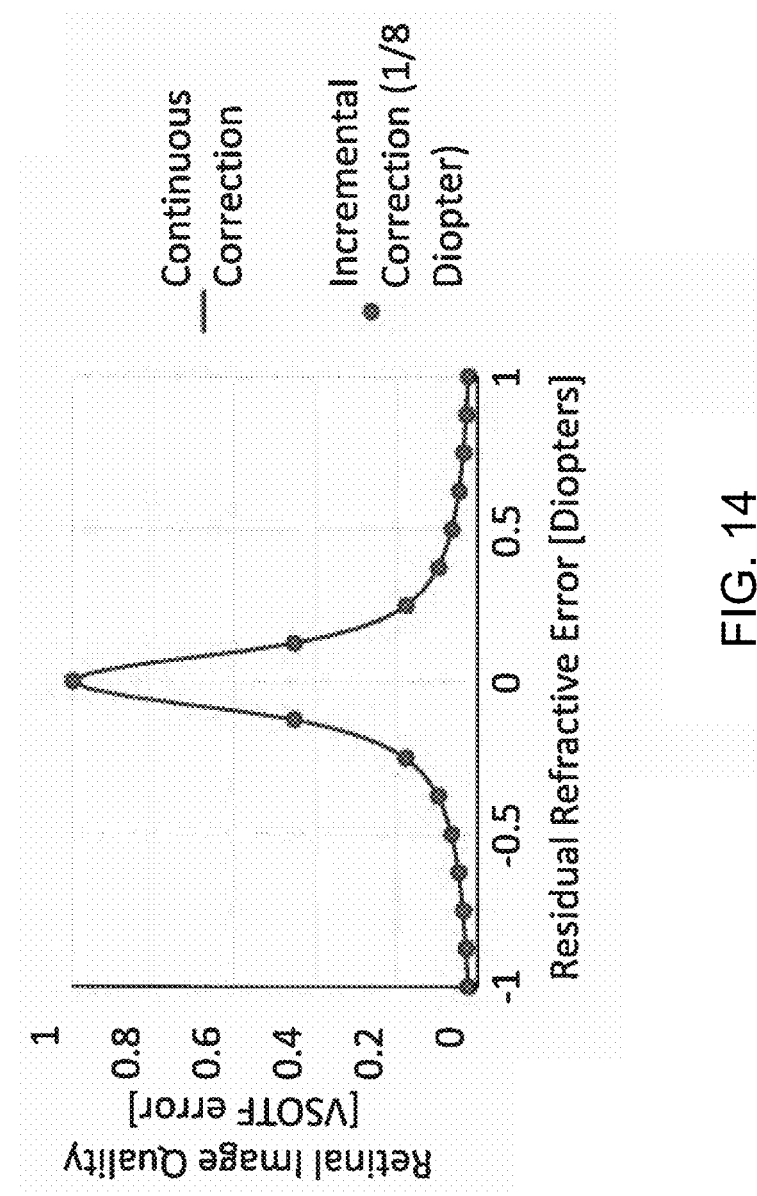
FIG. 14 shows the impact of refractive error on retinal image quality.
Figure 16A:
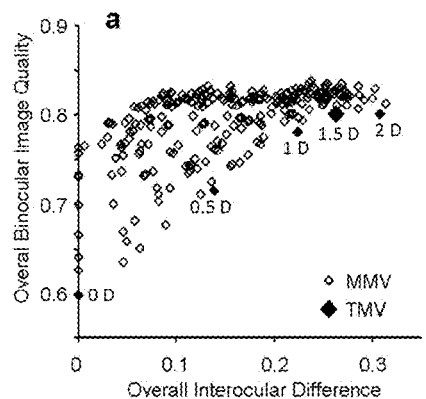
FIGS. 16a-16f show various binocular monovision corrections.
Figure 16B:
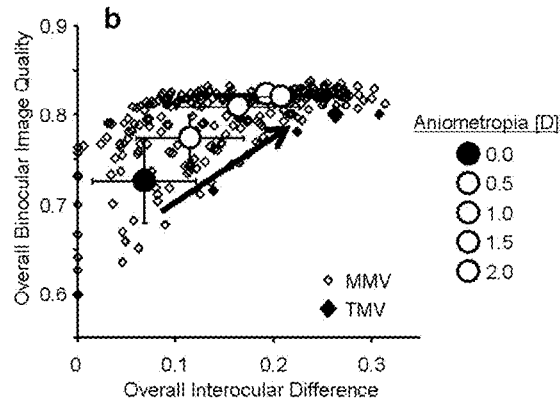
Figure 16C:
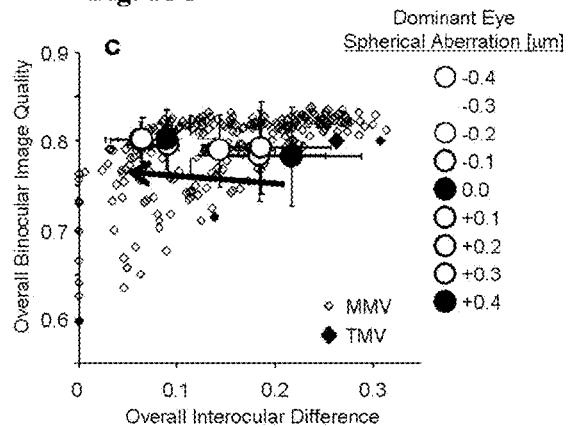
Figure 16D:
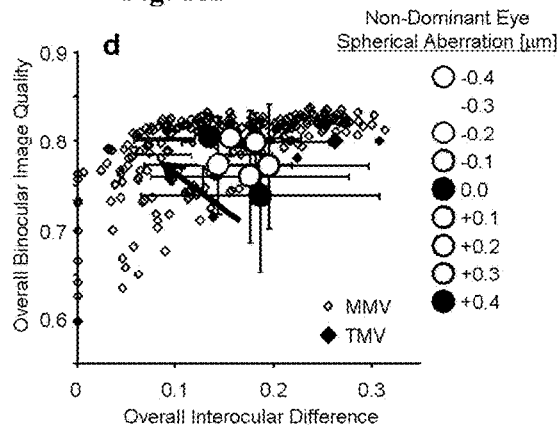
Figure 16E:
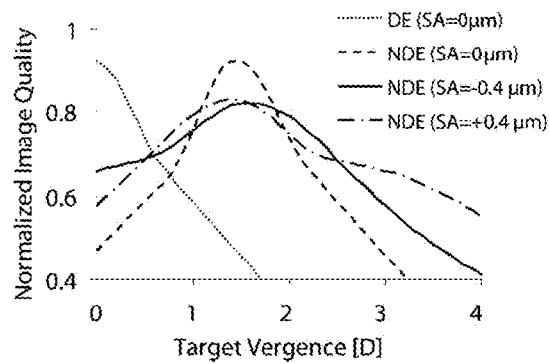
Figure 16F:
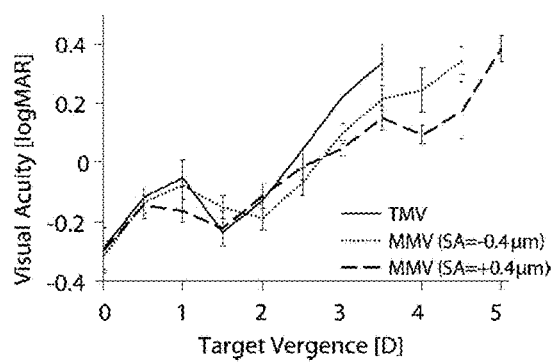

In one embodiment, laser induced refractive index changes by focused femtosecond laser pulses in optical tissues, or in an intraocular lens or contact lens or corneal inlay, as described herein may be performed to implement improvements in binocular visual performance in a presbyopia-correction approach known as modified monovision, by extending depth of focus by inducing different higher order aberrations, e.g., spherical aberration, to each of a patient's two eyes. As described in US 2012/0123534 and Zheleznyak, et al. "Modified Monovision With Spherical Aberration to Improve Presbyopic Through-Focus Visual Performance Modified Monovision With Spherical Aberration." *Investigative ophthalmology & visual science* 54.5 (2013): 3157-3165, e.g., the disclosures of which are incorporated by reference herein in their entireties, by extended the depth of focus of each eye, the optical quality of the 2 eyes becomes more similar, which facilitates neural functions like stereopsis and binocular summation. See also FIGS. 16a-16f, wherein FIG. 16a depicts overall binocular image quality as a function of overall interocular difference in image quality for all modified monovision (MMV) designs (gray diamonds). Traditional monovision (TMV) for 1.5 D anisometropia is represented by the large black diamond. TMV with remaining anisometropia is represented by the small black diamonds. Modified monovision designs were grouped by degree of anisometropia (FIG. 16b), dominant eye spherical aberration (FIG. 16c), and non-dominant eye spherical aberration (FIG. 16d). Error bars represent the standard deviation within each group of designs. Bold black arrows indicate the impact of the magnitude of increasing anisometropia or spherical aberration. In FIG. 16e, theoretical simulation of through-focus image quality for the dominant eye (DE) and nondominant eye (NDE) with SA=0, −0.4, and +0.4 micrometer is depicted. The DE was aberration-free. In the case of SA in the NDE, defocus was added to bring peak image quality to 1.5 D of anisometropia. In FIG. 16f, through-focus VA for traditional (TMV) and modified monovision (MMV) with ±0.4 micrometer of SA is depicted. This is preferable to traditional monovision where the 2 eyes have quite different optical quality. Employing laser induced refractive index changes by focused femtosecond laser pulses to correct such higher order aberrations in one or both eyes of a patient (as well as lower order aberrations) is particularly advantageous in such embodiment, as it does not change the optical tissue surface, and the results are thus less dependent upon regrowth of tissue cells, and the relatively small focus spot (e.g., approximately 1 micrometer diameter) allows for finer correction to be obtained. Laser induced refractive index changes by focused femtosecond laser pulses further advantageously enables a continuous range of correction (e.g., not limited to ⅛ diopters steps, as even a refractive error of ⅛ diopter can significantly reduce retinal image quality—see the impact of less precise corrections shown in FIG. 14), further advantageously enabling finer higher order aberration corrections to desired degrees.

In particular embodiments, laser induced refractive index changes by focused femtosecond laser pulses in optical tissues or optical polymers may be used to write a diffractive multifocal pattern to provide near, intermediate and/or far foci or to increase an eye's depth of focus (e.g., write a Fresnel lens pattern w/half wave phase change), or write a refractive multifocal for the same effects. A refractive multifocal may include multiple concentric rings of differing refractive power or segments of differing refractive power. Different multifocals may be used in combination for a binocular modified monovision presbyopia correction.

Additional details on modified monovision, including stereopsis data and theoretical treatment, are discussed in Zheleznyak, Leonard A., *Overcoming presbyopia by manipulating the eyes' optics*, Diss. University of Rochester, 2014 (Chapter 5); in Sabesan, Ramkumar, Len Zheleznyak, and Geunyoung Yoon "Binocular visual performance and summation after correcting higher order aberrations," *Biomedical optics express* 3.12 (2012): 3176-3189; and in Zheleznyak, Len, et al., "The role of sensory ocular dominance on through-focus visual performance in monovision presbyopia corrections." *Journal of vision* 15.6 (2015): 17-17. Such features as described therein may further be achieved by employing laser induced refractive index changes by focused femtosecond laser pulses in optical tissues to correct for higher order aberrations in accordance with the present disclosure. Conventional corneal or lens-based optical features often induce other aberrations and/or cause glare, halos and other dysphotpsias based in part on light scattering from surface patterns or healing response by the cornea or epithelium which may alter the intended correction, and so forth. In particular, current LASIK corneal treatments cannot create sharp edges as they are both formed with larger laser spot sizes and then have the cornea and/or epithelium healing over the surface ablations and flaps, thereby causing a change in the resulting corneal correction. The subsurface refractive index changes described herein do not suffer from these types of surface and healing issues, and therefore they demonstrate reduced incidence or amplitude of glare, halo, aberration induction, etc.—such relative reductions as compared to similar conventional treatments or optical designs being 10%, 20% 30% or more in the laser induced refractive change applications. Further, even in the cornea, current embodiments disclosed herein may provide corneal presbyopia treatments via multifocal diffraction patterns, for example, that will not suffer significant alteration from corneal or epithelial remodeling and healing, as laser induced refractive index change does not require incisions, flaps and ablation with their attendant healing issues.

Monocular Corrections

Employing laser induced refractive index changes by focused femtosecond laser pulses may further advantageously be employed to make customized monocular corrections, such as for lower order (sphere and cylinder (astigmatism and mixed astigmatism)) and higher order aberrations (such as coma, trefoil, spherical aberrations, etc.), as well as chromatic aberrations. Such combined corrections may be made in one layer or in two or more separate layers (e.g., or to correct such higher order aberrations in one or both eyes of a patient). In conventional treatments, whether in the cornea or in an optical polymer lens, there is limited number of surfaces to make the changes—i.e. in the cornea there is typically only the flap bed to make changes on, and in IOLs or contacts there is only one or two surfaces to work on. In the laser induced refractive index changes disclosed herein, as the changes can be done in one or more subsurface layer, different corrections can be added together in one or more layers—thereby expanding the options for corrections, and even allowing for multiple treatments over time to continue to fine tune vison correction, or even to respond to changing vision over time due to presbyopia and other vison issues. In particular embodiments, e.g., laser induced refractive index changes by focused femtosecond laser pulses may be used for monocular corrections such as for correcting aberrations for keratoconus (where the cornea becomes progressively thinner, ultimately bulging outward in the shape of a cone), or for aphakia (absence of the lens of the eyes), e.g., by providing approximately 20 diopter correction in the cornea or a polymer lens. With the extreme corneal surface shapes often found in keratoconous, a contact lens or scleral lens for such individuals may need to have a rather extreme matching back surface to fit correctly. This can cause additional optical aberrations and difficulties creating good vision through such lenses. In such cases, corneal corrections and/or corrections in a contact lens or IOL may be made via laser induced refractive index change to address these issues, including countering the optical effects of a contact lens or scleral lens.

Intraocular Telescope: Changing Ocular Magnification

Intraocular telescope lens for low vision condition corrections, such as for patients with macular degeneration, have been proposed such as described, e.g., in U.S. Pat. Nos. 6,596,026, 7,186,266 and Peli, "The optical functional advantages of an intraocular low-vision telescope," Optometry & Vision Science 79.4 (2002): 225-233, the disclosures of which are incorporated by reference herein in their entireties. In such systems, positive and negative lens elements are inserted into the eye spaced along the main optical axis, such that a magnified image provided by such telescoping lens combination enables the patient to use a peripheral part of the retina in combination with the fovea. While the resolution is much lower in the peripheral part than in the fovea due to larger photoreceptors, lower photoreceptor density and larger ganglion cell receptive fields, by increasing the magnification for peripheral vision for such low vision patients, visual performance is improved.

Figure 10:
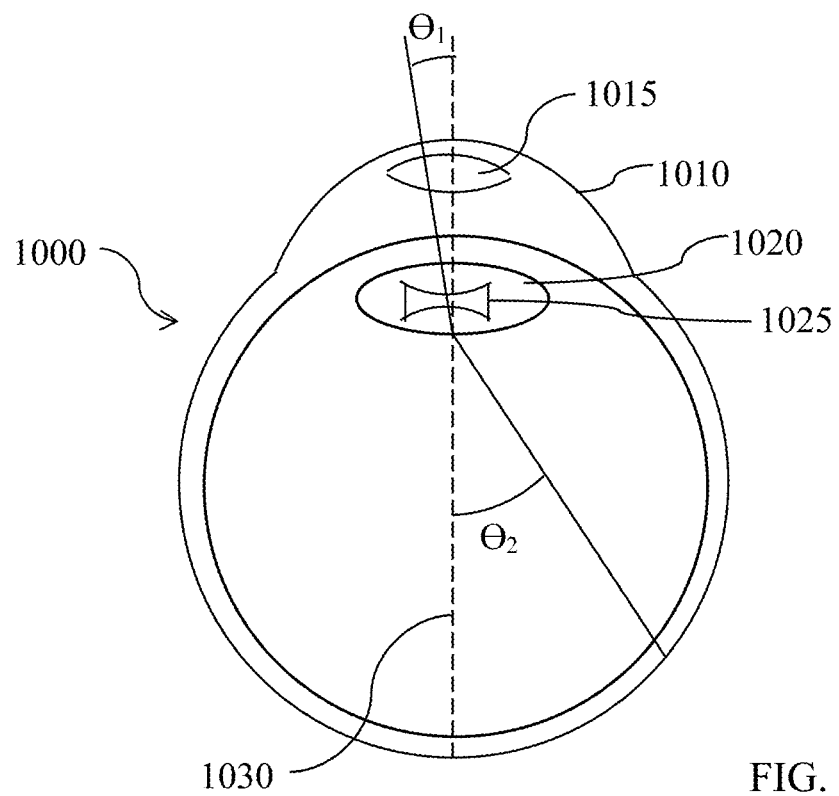
FIG. 10 shows a drawing illustrating an exemplary intraocular telescope system comprising positive and negative lens element refractive structures written into the cornea and crystalline lens.

In one embodiment of the present disclosure, laser induced refractive index changes by focused femtosecond laser pulses in optical tissues, or in an intraocular lens or contact lens, as described herein may be performed to implement such an intraocular telescopic lens effect by, e.g., laser writing a positive power lens in the cornea and a negative power lens in the natural crystalline lens (or in an inserted intraocular lens), in an ocular globe 1000 as show in FIG. 10 (with respect to positive power lens 1015 written in the cornea 1010 and negative power lens 1025 written in the natural crystalline lens 1020, aligned along optical axis 1030). Such telescopic lens effect may divert an image to a peripheral part of the retina (e.g., from angle $\Theta_1$ to $\Theta_2$ as illustrated). Alternatively, an intraocular lens having such a negative power lens element already written therein could be inserted in the eye, in combination with writing the positive power lens in the cornea using laser induced refractive index changes by focused femtosecond laser pulses. The ability to focus a femtosecond layer at different depths advantageously enables the positive and negative lens elements to be formed in the respective ocular tissues.

Slowing Myopia Progression

There is a worldwide epidemic of myopia development, especially in children and adolescents. The cause of myopia is mostly due to axial elongation of the eye, i.e. the eye's axial growth is not properly regulated and the myopic eyes grow too "long". One hypothesis for the cause of myopia development is that the optical quality on the peripheral retina is a trigger for axial length eye growth. It has been shown that by putting myopic defocus on the peripheral retina, the rate of eye growth slows. Multifocal optics may be used to minimally affect foveal vision (or vision near the visual axis of the eye that lands on or near the fovea of the retina) while placing myopic defocus on the peripheral retina, such as described, e.g., in Aller, Thomas A., Maria Liu, and Christine F. Wildsoet. "Myopia Control with Bifocal Contact Lenses: A Randomized Clinical Trial." *Optometry and vision science: official publication of the American Academy of Optometry* (2016), and in U.S. 2016/0062143, the disclosures of which are incorporated by reference herein in their entireties.

Figure 11:
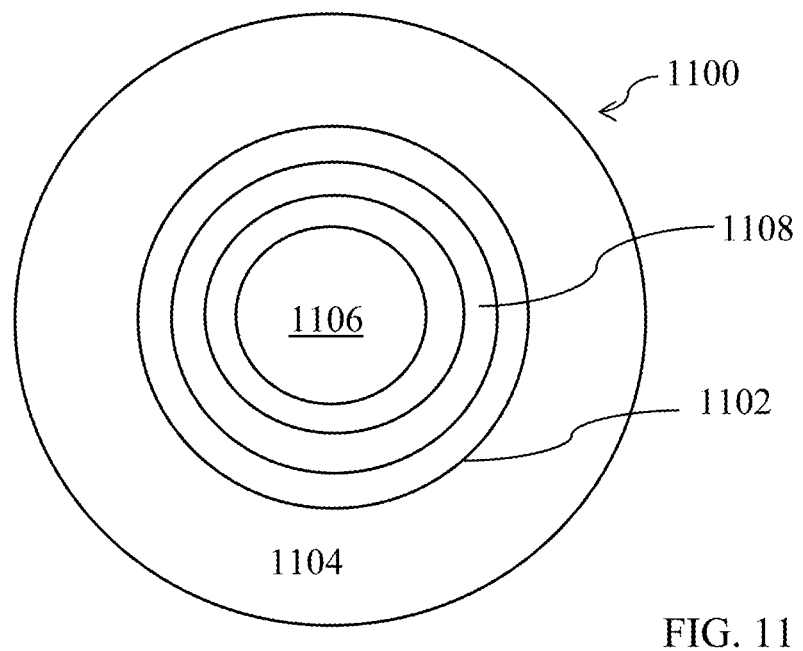
FIG. 11 shows a drawing illustrating a multifocal power profile that may be written into the cornea or natural crystalline lens, or an intraocular lens, to provide at least one peripheral zone having a different dioptric power around a center zone.
Figure 11A:
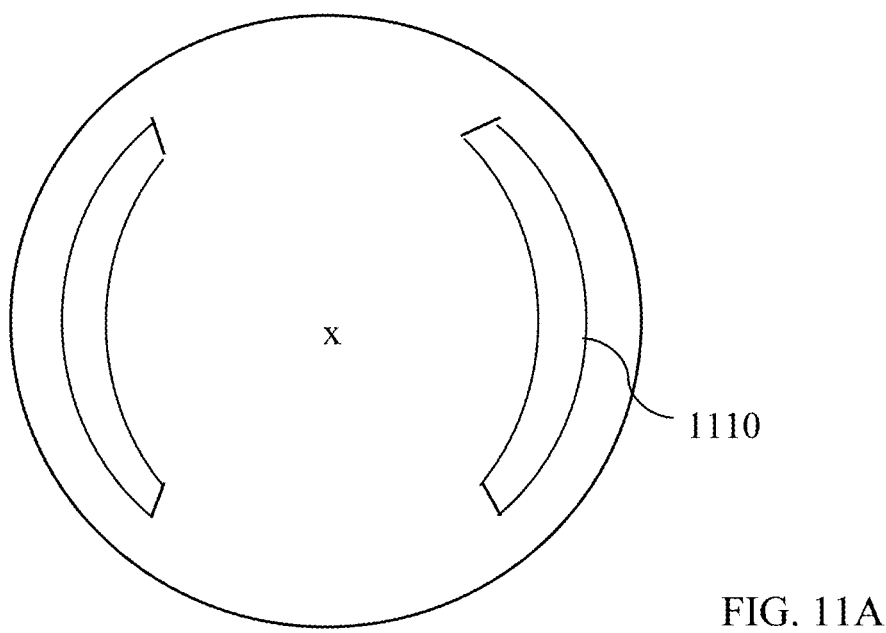
FIGS. 11a-11b show drawings of a lens having peripheral regions of different power in arcs or partial circles.
Figure 11B:
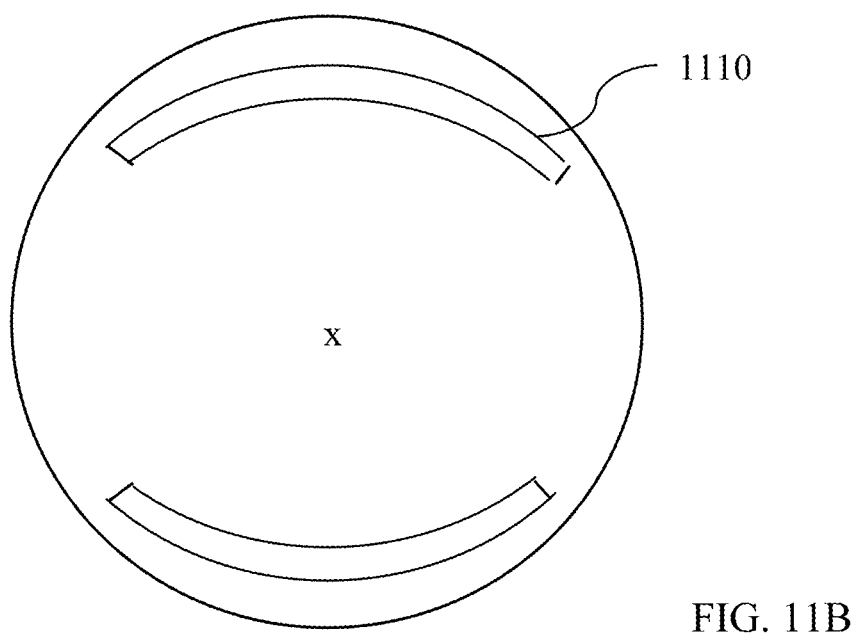

In one embodiment of the present disclosure, laser induced refractive index changes by focused femtosecond laser pulses in optical tissues, or in an intraocular lens, corneal inlay or contact lens, as described herein may be performed to implement such a peripheral myopic defocus or a multifocal effect for use in preventing and/or slowing myopia progression, by, e.g., laser writing at least one peripheral zone having a different dioptric power around a center zone of the cornea or natural crystalline lens, or of an intraocular lens, contact lens or inlay, so as to provide a multifocal power profile in the cornea or lens, such as shown in FIG. 11. More particularly, there is illustrated a diagrammatic view of a plane view of a cornea surface into which a multifocal power profile 1100 has been written. The multifocal power profile comprises an optic zone 1102 and an outer zone 1104. The optic zone 1102 comprises a first, central zone 1106 and at least one peripheral zone 1108, wherein central zone 1106 is written to provide a desired degree of dioptric power for foveal vision correction, and peripheral zone 1108 is written to provide a change in refractive index putting a myopic defocus on the peripheral retina. In specific embodiments, the diameter of the optic zone 1102 may be selected to be, e.g., about 6 to 10 mm, the diameter of the substantially circular first zone 1106 may be selected to be about 3 to 5 mm, and the boundary diameters of an annular outer peripheral zone 1108 may be selected to be between such optic zone and central zone boundaries, and about 1-2 mm wide as measured from the inner peripheral zone bounder to the outer peripheral zone bounder relative to the center of the central zone. While the outer boundary of the at least one peripheral zone 1108 does not necessarily coincide with the outer margin of the optic zone 1102 in FIG. 11, in other exemplary embodiments they may coincide. While FIG. 11 is described in context of refractive index changes written into the cornea, in other embodiments the changes may be written into an intraocular lens or a contact lens. When written into a lens, the outer zone 1104 surrounding the optic zone 1102 may provide standard lens features, including lens positioning and centration. In accordance with one exemplary embodiment, e.g., the outer zone 1104 may include one or more stabilization mechanisms to reduce lens rotation when on eye. While the various zones in FIG. 11 are illustrated as concentric circles, the zones may comprise any suitable round or non-round shapes such as an elliptical shape. Such zones may also comprise arcs or partial circles 1110 (for example one or more 30-120 degree arcs set, and as a further example two such arcs set symmetrically either above and below the optical axis x or left and right of the optical axis x), as shown in FIGS. 11a-11b.

As the entrance pupil size of the eye and target vergence/accommodation varies among subpopulations, the peripheral refractive profile or the multifocal power profile design may be customized to achieve both good foveal vision correction and myopic treatment efficacy based on the patient's average pupil size and preferred target vergence. Moreover, as pupil size correlates with refraction and age for pediatric patients, in certain exemplary embodiments, the peripheral correction or multifocal power profile or lens may be further optimized towards subgroups of the pediatric subpopulation with specific age and/or refraction based upon their pupil sizes. Essentially, the power profiles may be adjusted or tailored to pupil size to achieve an optimal balance between foveal vision correction, axial length and growth of the eye, increased depth of focus, and reduced sensitivity. The use of a femtosecond laser to write a desired power profile directly into optical tissue such as cornea or lens tissue, or into an inserted intraocular lens or a contact lens, is especially advantaged as it can be customized to provide individually desired power profiles and to further adjust the peripheral refractive or multifocal power profile as the eye continues to grow as needed to further prevent and/or slow myopia progression. Further, for corneal corrections employing such multifocal or peripheral defocus treatments, later treatments or corrections may be designed to reverse the peripheral defocus as the eye stabilizes or axial growth slows or ceases, e.g. the peripheral defocus can be reduced or removed all together in such later treatments.

Apodized Multifocal Diffractive Patterns

Intraocular lenses that provide near and far foci are described in U.S. Pat. No. 7,572,007, the disclosure of which is incorporated by reference in its entirety, where the lens includes an optic having an anterior surface and a posterior surface, where the optic provides a far focus and a diffractive structure comprising a plurality of diffractive zones is disposed on at least one of those surfaces so as to provide a near focus. In such lenses, each zone is separated from an adjacent zone by a zone boundary that imparts an optical phase delay to incident light (e.g., visible incident light of from about 400 nm to about 700 nm), and wherein at least two consecutive zone boundaries (two zone boundaries separating one common diffraction zone from two different zones) are configured such that a difference between their associated phase delays for at least one wavelength of the incident light (e.g., about 550 nm) is greater than about $1/20$ wavelength and preferably greater than about $1/4$ wavelength, preferably in a range from about $1/20$ wavelength to about 1 wavelength, so as to direct a portion of the incident light to a location between the near and far foci. In a related aspect, the zone boundaries may comprise a plurality of steps, where at least two consecutive steps exhibit a differential height adapted to provide a difference greater than about $1/20$ wavelength, and preferably greater than about $1/4$ wavelength, e.g., in a range of about $1/20$ wavelength to about 1 wavelength, in their associated phase delays. In another aspect, in the IOL having a plurality of steps as zone boundaries of its diffractive structure, a portion of the steps may exhibit decreasing heights as a function of increasing distance from the center of the surface on which the diffractive structure is disposed, that is, a portion of the step heights are apodized to provide intermediate vision and/or to change the relative proportions of light rays going to the different foci. Such diffractive IOLs are said to provide enhanced intermediate vision, without any significant degradation of the far and near vision.

In one embodiment of the present disclosure, laser induced refractive index changes by focused femtosecond laser pulses in optical tissues, or in an intraocular lens or contact lens, as described herein may be performed to implement such diffractive structure by writing structures with different refractive indexes to form the plurality of diffractive zones (directly into ocular tissues, or into an intraocular or contact lens or corneal inlay—i.e. inside and below the surface of the cornea or optical material) where each zone is separated from an adjacent zone by a zone boundary that imparts an optical phase delay to incident light (e.g., visible incident light of from about 400 nm to about 700 nm), and wherein at least two consecutive zone boundaries (two zone boundaries separating one common diffraction zone from two different zones) are configured such that a difference between their associated phase delays for at least one wavelength of the incident light (e.g., about 550 nm) is greater than about 1/20 wavelength and preferably greater than about 1/4 wavelength, preferably in a range from about 1/20 wavelength to about 1 wavelength, so as to direct a portion of the incident light to a location between the near and far foci, to provide enhanced intermediate vision, without any significant degradation of the far and near vision. The use of a femtosecond laser to write such a diffractive element profile directly into optical tissue such as cornea or lens tissue, or into an inserted intraocular lens, is especially advantaged as it can be customized to provide individually designed diffractive element patterns to obtain individually desired degrees of enhanced intermediate vision correction, and further in relation to lifestyle requirements (for example a preference for reading, or computer work, or distance vision) and/or pupil dynamics.

Rotationally Symmetric and Asymmetric Diffractive Structures

Ophthalmic lenses, such as intraocular lenses or contacts, having at least one rotationally symmetric single ring microstructure or diffractive structure coupled thereto or integrated thereon are described in U.S. Pat. Nos. 8,430,508 and 8,480,228, the disclosures of which are incorporated herein by reference in its entirety. Such lenses may include a single or limited number (e.g., less than four) of rotationally symmetric diffractive echelettes that provide for an extended depth of focus. In one embodiment of the present disclosure, laser induced refractive index changes by focused femtosecond laser pulses in optical tissues, or in an intraocular lens or contact lens, as described herein may be performed to implement such a rotationally symmetric diffractive structure or single ring microstructure by writing rotationally asymmetric diffractive structures directly inside ocular tissues, or inside an intraocular or contact lens. The use of a femtosecond laser to write such structures directly into optical tissue such as cornea or lens tissue, or into an inserted intraocular lens or contact lens, is especially advantaged as it can be customized to provide individually designed diffractive element patterns to obtain individually desired degrees of enhanced depth of focus.

Ophthalmic lenses, such as intraocular lenses, having at least one rotationally asymmetric diffractive structure coupled thereto or integrated thereon are described in U.S. Pat. No. 8,894,204, the disclosure of which is incorporated by reference in its entirety. Such lenses may include a single or limited number (e.g., less than four) of rotationally asymmetric diffractive echelettes that provide for an extended depth of focus. More particularly, such lenses may include an optic having at least a toric portion for correcting astigmatism and having a base cylinder power, and a rotationally asymmetric, single or limited number of diffractive echelettes for extending depth of focus. The rotational asymmetry may be with respect to the shape of the single or limited diffractive echelette(s) with respect to the optical axis. In other words, rather than have a concentric echelette(s) in the shape of a circle, the echelette(s) may be in the shape of an ellipse, or any other shape that is rotationally asymmetric with respect to the optical axis. The rotational asymmetry may also be the result of a variable stepheight along the echelette(s), as shown in for example U.S. Pat. No. 8,444,267, the disclosure of which is incorporated herein by reference in its entirety. In standard diffractive IOLs the echelette stepheight remains constant, although the stepheight between echelettes may vary. Here, in a single echelette embodiment for example, the stepheight may vary tangentially as a function of the rotational angle. The extended depth of focus accomplished by the rotational asymmetry may reduce sensitivity of the optic to at least one of rotation and the base cylinder power. Additionally, the rotational asymmetry may result in a differential depth of focus along predetermined meridians.

In one embodiment of the present disclosure, laser induced refractive index changes by focused femtosecond laser pulses in optical tissues, or in an intraocular lens or contact lens, as described herein may be performed to implement such a rotationally asymmetric diffractive structure by writing rotationally asymmetric diffractive structures directly into ocular tissues, or into an intraocular or contact lens. The use of a femtosecond laser to write such rotationally asymmetric diffractive structures directly into optical tissue such as cornea or lens tissue, or into an inserted intraocular lens, is especially advantaged as it can be customized to provide individually designed diffractive element patterns to obtain individually desired degrees of enhanced depth of focus. These symmetric or asymmetric single ring microstructures and limited number diffractive echelette patterns for extended depth of focus are not available and likely cannot be made available in conventional corneal laser treatments due to the imprecision of current laser approaches (i.e. LASIK) and the eye's normal healing responses to such surface treatments. Similarly, conventional contact lenses would not likely work well with a single ring surface structure, as it may be irritating to the eye and/or the microstructures may get filled in with tear film components or debris. Finally, there is no way to create these structures or fine tune them inside the eye in an IOL using conventional surface structure approaches. In each case, laser induced refractive index change to create these structures inside the cornea or contact lens or IOL is the way to realize the benefits of these extended depth of focus structures in each of these example cases.

Multifocal Diffractive Structures

Ophthalmic lenses, such as intraocular lenses, having at least two annular zone lenses and an optical step provided between annular zone lenses are described in U.S. Pat. No. 6,120,148, the disclosure of which is incorporated by reference in its entirety. Alternately, a different multifocal diffractive lens is described in U.S. Pat. No. 7,377,640, the disclosure of which is incorporated by reference herein in its entirety. Usually, a diffractive lens consists of any number of annular lens zones of equal areas, so-called Fresnel zones. At the common border of adjacent Fresnel zones usually $+\lambda/2$-steps or $-\lambda/2$-steps are introduced between all zones, $\lambda$ being the so-called design wavelength, in order to provide for constructive interference of light waves in the 0th and 1st diffractive order, or the 0th and $-1$-st diffractive order, respectively. Also, diffractive lenses are known in which the steps between adjacent zones are any odd integer half of the design wavelength. Besides designs in which the optical steps between zones are always positive or negative, designs with +λ/2-steps and −λ/2-steps between subsequent adjacent zones are known. In such lenses, constructive interference of light waves takes place predominantly in the −1st and/or +1st diffractive order.

In accordance with one form of diffractive lenses described in U.S. Pat. No. 6,120,148, a multifocal diffractive lens includes at least two annular zone lenses. Provided between adjacent annular zone lenses is an optical step. Each annular zone lens exhibits a refractive power profile $D_g,i(r)$ wherein i is any i-th annular zone lens and r is the distance between an axis of the diffractive lens and a point on a back surface of the lens. The lens is further characterized in that an average power of zones i,j . . . are given by $D_{av},i$, $D_{av},j$ . . . respectively, and optical path lengths of light rays extending from an object point to a conjugated image point are different by the optical step for light rays transmitting through adjacent annular zone lenses. The annular zone lenses are shaped and positioned such that all of the average refractive powers $D_{av},i$, $D_{av},j$ . . . are essentially equal to a single value, $D_a,v$.

Figures 15A, 15B:
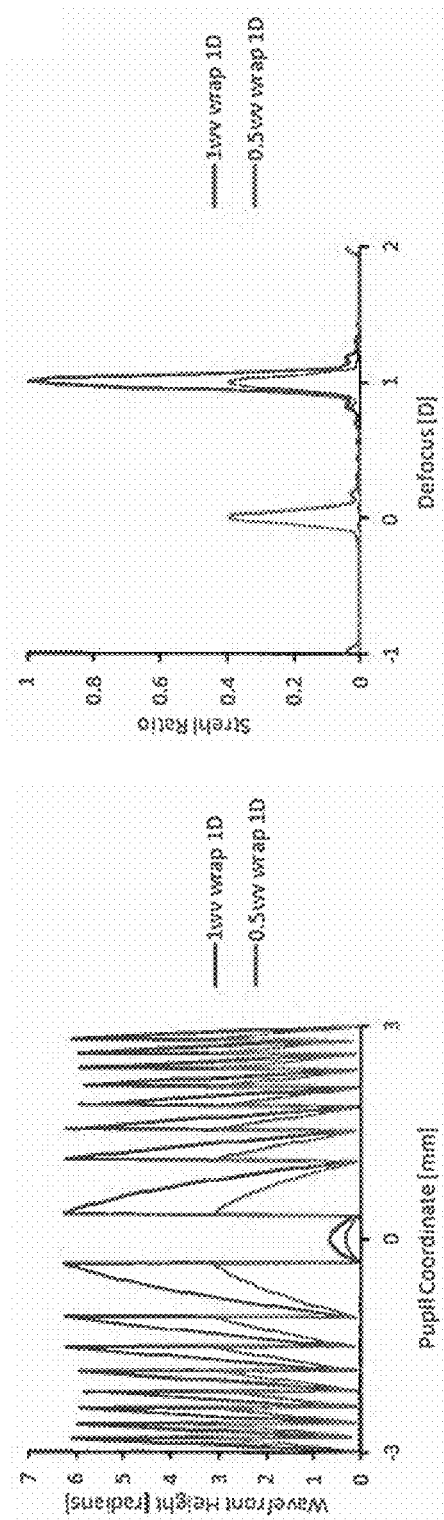
FIGS. 15a and 15b show multifocal through-focus image quality from a diffractive wavefront pattern.

In one embodiment of the present disclosure, laser induced refractive index changes by focused femtosecond laser pulses in optical tissues, or in an intraocular lens or contact lens or corneal inlay, as described herein may be performed to implement such a multifocal diffractive lens structure by writing multiple annular zone diffractive structures directly into ocular tissues, or into an intraocular or contact lens material. The use of a femtosecond laser to write such multiple annular zone diffractive structures directly into optical tissue such as cornea or lens tissue, or into an inserted intraocular lens, is especially advantaged as it can be customized to provide individually designed diffractive element patterns to obtain individually desired degrees of correction. These diffractive multifocal patterns are not available and likely cannot be made available in conventional corneal laser treatments due to the imprecision of current laser approaches (i.e. LASIK) and the eye's normal healing responses to such surface treatments. Similarly, conventional contact lenses do not work well with diffractive surface structure, as they may be irritating to the eye and/or they may get filled in with tear film components or debris. Finally, there is no way to create these structures or fine tune them inside the eye in an IOL using conventional surface structure approaches. In each case, laser induced refractive index change to create these diffractive structures inside the cornea or contact lens or an IOL is the way to realize the benefits of these multifocal structures in each of these example cases. Using a Fresnel lens approach with phase wrapping, multifocality can be achieved using a half-wave height or phase change as shown in FIGS. 15a and 15b. Additionally, for a full wave height or phase change, a monofocal correction is maintained but with greater optical power compressed into a Fresnel lens approach, again as shown in FIGS. 15a and 15b, which demonstrate multifocal through-focus image quality from a diffractive wavefront pattern.

Multifocal Refractive Structures

Multifocal ophthalmic lenses, such as intraocular lenses, having a plurality of alternating power zones with a continuously varying power within each zone (e.g., from near correction focal power to far correction focal power), as well as a continuous transition from one zone to another, are described in U.S. Pat. No. 4,898,461, the disclosure of which is incorporated by reference in its entirety. In a first version, continuous alternating power variation is accomplished by a continuously changing curvature of the lens posterior surface, thereby altering the angle of impact of light rays on the eye. In a second version, continuous alternating power variation is accomplished by creating non-homogenous surface characteristics having refractive material indexes which continuously vary in the lens radial direction out from the optical axis.

In one embodiment of the present disclosure, laser induced refractive index changes by focused femtosecond laser pulses in optical tissues, or in an intraocular lens or contact lens or corneal inlay, as described herein may be performed to implement such a continuous alternating power variation between a plurality of alternating power zones by writing a continuously varying GRIN layers formed directly into ocular tissues, or into an intraocular or contact lens material. The use of a femtosecond laser to write such continuously varying alternating power zones directly into optical tissue such as cornea or lens tissue, or into an inserted intraocular lens, is especially advantaged as it can be customized to provide individually designed GRIN layer patterns to obtain individually desired degrees of multifocal correction.

Multifocal Structures with Controlled Image Quality and Light Intensity

Multifocal ophthalmic lenses, such as intraocular lenses, with multiple zones providing near and far vision correction, having improved image quality and light intensity for near images are described in U.S. Pat. No. 5,225,858, the disclosure of which is incorporated by reference in its entirety. This can be accomplished by maintaining the near vision correction power of appropriate zones of the lens substantially constant for a major segment of the near vision correction power region of each zone and by providing a central zone having an increased depth of focus. More particularly, for near vision, the working distance, i.e., the distance between the eye and the object, can usually be varied with relative ease as when a person reading adjusts the distance between his eyes and the material being read. For this reason, it may be desirable to concentrate as much light as possible at a single near location to provide maximum image quality at such near location This is accomplished by the major segments of each near vision correction power region which have substantially constant near vision correction power. Although this inherently reduces the depth of focus at such major segments, this is typically immaterial at this near location because of the ability to easily adjust the working distance. It further may be desirable to space the near vision correction power regions radially outwardly from the central zone of the lens. This can be accomplished by providing the multifocal ophthalmic lens with a plurality of annular zones circumscribing an optical axis with each of first and second of the annular zones having a far vision correction power and a region with a near vision correction power. The vision correction power between the far and near vision correction powers is progressive. Each of the regions has a major segment in which the near vision correction power is substantially constant. This provides improved image quality and light intensity for near images and less intensity for intermediate images where image quality is of less importance.

More particularly, a multifocal ophthalmic lens adapted for implantation in the eye or to be disposed on or in the cornea is described, wherein the lens has an optical axis, a central zone and a plurality of annular zones circumscribing the central zone. Two of the annular zones have a first region with a far vision correction power and a second region with a near vision correction power. In an IOL embodiment, the vision correction power between far and near is progressive, and each of the second regions has a major segment in which the near vision correction power is substantially constant, and the power in the central zone varies.

In one embodiment of the present disclosure, laser induced refractive index changes by focused femtosecond laser pulses in optical tissues, or in an intraocular lens or contact lens or corneal inlay, as described herein may be performed to implement such a multifocal power variation between a central and plurality of annular zones by writing one or more GRIN layers formed directly into ocular tissues, or into an intraocular or contact lens material, to form the desired refractive properties for the central and annular zones. The use of a femtosecond laser to write such GRIN layer forming desired zones directly into optical tissue such as cornea or lens tissue, or into an inserted intraocular lens, is especially advantaged as it can be customized to provide individually designed GRIN layer patterns to obtain individually desired degrees of multifocal correction.

Multiple Phase Plates

In diffractive ophthalmic lenses, the optic area is generally divided into a plurality of annular zones or echelettes that are offset parallel to the optical axis by predetermined step heights to provide a specific phase relationship between the zones. The term "zone plate" or "phase plate" as used generally in the art is defined to be a pattern of concentrically arranged annular zones which is characterized, at least in part, by the step height between zones, the circumferential spacing between zones, and the surface profile of each zone. Zone plates are usually configured to maintain a predefined phase relationship of light passing through the zones.

In one approach, a phase plate or zone plate comprises a plurality of zones in which the optical height of the steps (i.e., the physical height times the difference between the refractive index of the material and the refractive index of the surrounding media) between the individual zones is one-half that of light at a design wavelength in the visible range. In such designs, approximately 80% of the light at the design wavelength is evenly split between zeroth and first diffraction orders, where the zeroth diffraction order is generally considered to be light that is un-diffracted or unaffected by the zone plate. This zone plate configuration is used to produce a bifocal lens in which (1) the zeroth diffraction order produces a first focus or focal point for distant vision and (2) the first diffraction order produces a second focus or focal point corresponding to near or intermediate vision. In addition, chromatic dispersion produced by the first diffraction order, which is usually opposite in sign to refractive chromatic dispersion, may be used to reduce the overall chromatic aberrations in the near vision focus, since the refractive and diffractive chromatic dispersions components tend to cancel one another. However, the distant vision focus does not benefit from this diffractive chromatic dispersion, since it comprises only light that is un-diffracted by the zone plate. Thus, the distance vision is purely refractive and receives no reduction in any chromatic aberrations induced by refractive chromatic dispersions.

A characteristic of ophthalmic lenses incorporating diffractive zones or phase plates is that the amount of light in the near and distant foci is substantially constant for all pupil sizes. It is desirable in certain instances to increase the amount of light in the distant focus as the pupil size increases, for instance under intermediate or low light conditions. One way to increase the amount of light dedicated to distance vision is to restrict the zone plate to the central portion of the lens and to make the outer region of the lens refractive only. Another approach is a diffractive lens comprising an apodization zone in which the step height between zones in the transition region is progressively reduced. The steps between zones are centered on a base curve BC so as to avoid sharp discontinuities in the resulting wavefront that can produce unwanted diffractive effects. In either of these designs, the outer refractive portion of the lens does not benefit from the use of diffractive power to reduce chromatic aberrations, potentially resulting in increased chromatic aberrations as the pupil size increases under lower lighting conditions.

One problem associated with multifocal/bifocal IOLs is the problem of halos. This problem manifests itself when light from the unused focal image creates an out-of-focus image that is superimposed on the used focal image. For example, if light from a distant point source or slightly extended source is imaged onto the retina of the eye by the distant focus produced by a bifocal IOL, the near focus produced by the IOL will simultaneously superimpose a defocused image on top of the image formed by the IOL's distant focus. This defocused image may manifest itself in the form of a ring of light surrounding the in-focus image produced by the IOL's distant focus.

Multifocal ophthalmic lenses using a combination of refraction and diffraction to provide improved performance of diffractive lenses, and in particular reducing the problem associated with halos manifesting when light from an unused focal image creates an out-of-focus image that is superimposed on the used focal image, are described in U.S. Pat. No. 7,188,949, the disclosure of which is incorporated by reference in its entirety. One disclosed aspect involves an ophthalmic lens comprising an optic having an anterior surface, a posterior surface, and an optical axis. The ophthalmic lens further comprises a first region having a first optical power and a second region having a second optical power. The first region comprises a multifocal phase plate configured for forming a first focus and a second focus, while the second region comprises a monofocal phase plate for forming a third focus. The monofocal phase plate and the multifocal phase plate are preferably disposed about at least one base curvature. In certain embodiments, the first region comprises a first base curvature having a finite first radius of curvature and the second region comprises a second base curvature having a finite second radius of curvature different from the first radius of curvature. The ophthalmic lens may further comprise a third region having a third optical power and comprising a third phase plate. For example, the third region may be an intermediate region that is disposed between the monofocal phase plate and the multifocal phase plate. In one embodiment the first region may be disposed in the center of the optic and the second region is disposed outside the first region. Alternatively, the second region is disposed in the center of the optic and the first region is disposed outside the second region. In either embodiment, the base curvature may have a shape that is spherical, parabolic, elliptical, hyperbolic, or some other aspherical shape. The first region may have a refractive optical power that is preferably greater than a diffractive optical power of the multifocal phase plate and the second region may have a refractive optical power that is preferably greater than a diffractive optical power of the monofocal phase plate. The monofocal phase plate and the multifocal phase plate may both be disposed on the anterior surface of the optic or on the posterior surface of the optic. Alternatively, the monofocal phase plate and the multifocal phase plate may be disposed on opposite surfaces of the optic.

In one embodiment of the present disclosure, laser induced refractive index changes by focused femtosecond laser pulses in optical tissues, or in an intraocular lens or contact lens or corneal inlay, as described herein may be performed to form such multifocal and monofocal phase plates by writing one or more GRIN layers formed directly inside ocular tissues, or inside an intraocular or contact lens or corneal inlay material, to form the desired multifocal and monofocal phase plates. The use of a femtosecond laser to write such GRIN layer forming desired zones directly into optical tissue such as cornea or lens tissue, or into a contact lens, or into an inserted intraocular lens, is especially advantaged as it can be customized to provide individually designed GRIN layer patterns to obtain individually desired degrees of multifocal correction.

Diffractive Zones with Varying Areas

Multifocal ophthalmic lenses are known for providing a near and far focus, as well as an intermediate focus, utilizing diffractive structures to direct incident light to three focal regions corresponding to near, intermediate and far vision. Such trifocal lenses, however, may suffer from a number of shortcomings. For example, they provide intermediate vision at the expense of degradation of the far and/or near vision. Multifocal ophthalmic lenses are described in U.S. Pat. No. 7,188,949, the disclosure of which is incorporated by reference in its entirety, which include a plurality of diffractive zones with varying areas so as to cause broadening of optical energy profiles at a near and a far focus generated by those zones, thereby creating an intermediate focus. In some cases, a maximum difference between the areas of the diffractive zones can be, e.g., in a range of about 75% to about 200%. In one aspect, a trifocal ophthalmic lens is disclosed that includes an optic having at least one optical surface, and a plurality of diffractive zones that are disposed on a portion of that surface about an optical axis of the optic. At least two of those diffractive zones have different areas so as to cause broadening of optical energy profiles at a near and a far foci of the diffractive zones for generating an intermediate focus. By way of example, the diffractive zones can direct at least about 25% of incident light energy, or preferably at least about 28% of the incident light energy, into each of the near and far foci, while directing at least about 10% of the incident light energy to the intermediate focus. The optical surface can also include a reference profile characterized by a base curve for generating a refractive power corresponding to the far focus. The term "diffractive zone," as used therein, refers to an area of the surface that contains one or more diffractive structures that are repeated, either identically or in accordance with a selected apodization, to generate a diffraction pattern disposed on that surface.

In one embodiment of the present disclosure, laser induced refractive index changes by focused femtosecond laser pulses in optical tissues, or in an intraocular lens or contact lens, as described herein may be performed to form such diffractive zones having different areas as described in U.S. Pat. No. 7,441,894 by writing one or more GRIN layers formed directly into ocular tissues, or into an intraocular or contact lens material, to form a desired multifocal optical lens structure, such that the zones collectively provide near, intermediate and far vision. The use of a femtosecond laser to write such GRIN layer forming desired zones directly into optical tissue such as cornea or lens tissue, or into an inserted intraocular lens, is especially advantaged as it can be customized to provide individually designed GRIN layer patterns to obtain individually desired degrees of multifocal correction.

Off-Axis Viewing

The various vision correction techniques described herein may be employed in combination with diffractive grating patterns written on or into a cornea or ophthalmic lens to provide off-axis viewing capabilities such as described in co-pending, commonly assigned PCT/US2016/034340, the disclosure of which is incorporated by reference herein in its entirety. In such systems, peripheral light from a peripheral light source may be diffracted by the diffraction grating so as to appear at about a same location as light from an ambient scene substantially in a direction of a central field of view, such that the eye sees simultaneously the peripheral light and the light from an ambient scene as superimposed, at least in part, over each other. Such diffractive gratings may be written by inducing refractive index changes by focused femtosecond laser pulses in optical tissues, or in an intraocular lens or contact lens or corneal inlay, as described herein in combination with the further refractive elements and structures described herein.

Correcting Optical Effects of the Physical Configurations of Contact Lenses or Intraocular Lenses.

Figure 12:
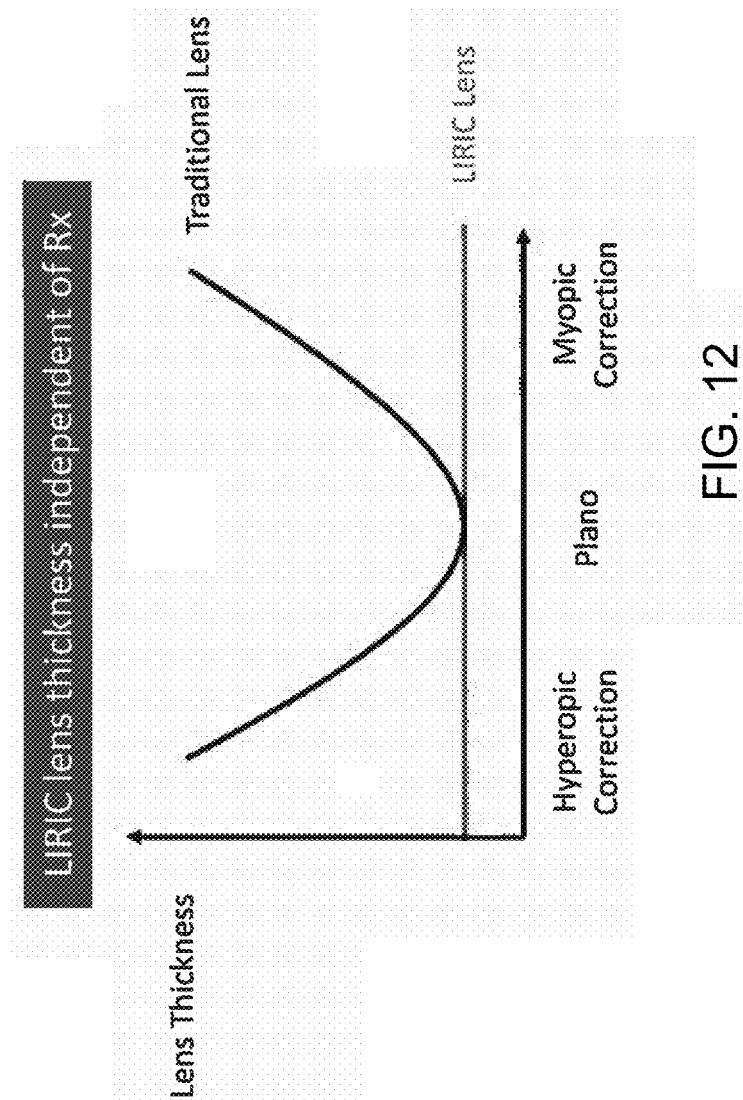
FIG. 12 shows the impact of contact lens power on lens thickness.
Figure 13:
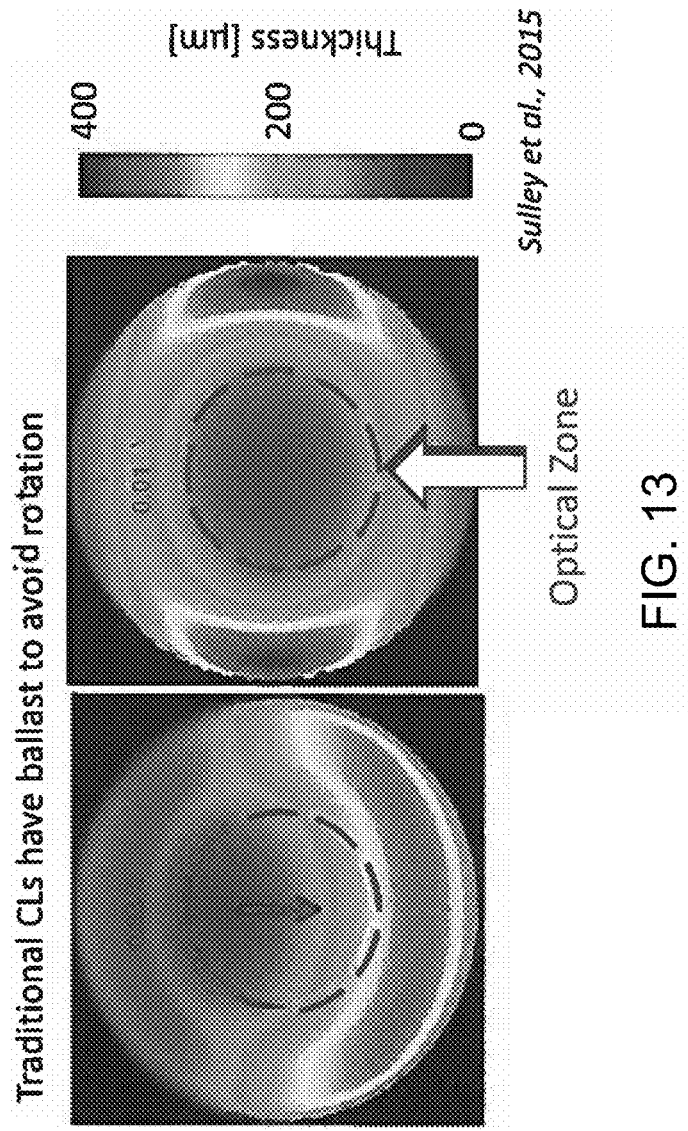
FIG. 13. Shows the optical impact of contact lens ballast.

FIGS. 12 and 13 demonstrate optical and eye health issues caused by the physical shape and ballast of contact lenses. In FIG. 12, it can be seen that contact lens thickness in conventional contacts is dependent on the diopter power. Particular parts of a contact lens increase with dioptric power (regardless of myopic or hyperopic correction), resulting in less oxygen transmission through the lens and compromised eye health, as thicker contact lenses have poor oxygen transmission. Further, contact lenses often use stabilization features to maintain the orientation of the contact lens relative to the eye, for example for rotationally asymmetric aberration corrections such as astigmatism, higher order aberrations or presbyopia corrections. Different stabilization features or designs may be used to keep the cylinder axis or other asymmetric visual corrections aligned with the eye. Some of these design features include prism ballast, peripheral ballast, thin zones (also known as double slab-off), posterior toric, chamfering, truncation, and combinations that incorporate multiple different design features into a single lens. These stabilization features are typically in the outer peripheral zone of the lens, but they may also be included partly in the central optical zone. Such stabilization features may cause aberrations or optical effects in the optical zone which can impact the visual acuity of the patient. See, e.g., FIG. 13, depicting ballast stabilization features which may add optical aberrations to the contact lens. Embodiments of laser induced refractive index change and subsurface phase changes described variously herein can be used to correct and counteract these issues. For example, in one embodiment, the refractive power of the contact lens can be increased within the contact lens to maintain a flatter lens even as myopic or hyperopic corrections get higher, for example, by including gradient refractive index Fresnel wavefronts inside the contact lens. In another embodiment to counteract the optical effects in a contact lens having ballast, a correcting optical element can be created inside the lens to counteract the optical effects of the ballast, either by reducing the optical power of the ballast area to match the rest of the contact lens, or by increasing the optical power of the non-ballast area to match that of the ballast area. In a particular embodiment, e.g., a contact lens having a prism ballast feature may be modified to include an opposite prism refractive element written in accordance with the present disclosure, to maintain the ballast effect while counter-acting the optical effect of the prism ballast. Such optical elements for counteracting the optical effects of the ballast may also be used in conjunction with diffractive multifocal IRIS phase change patterns inside the lens, as well as with IRIS phase change astigmatism, higher order aberration, presbyopia and visual field corrections. The combination of astigmatic corrections and multifocal elements in conventional contact lenses utilizing surface-based correctors causes significant problems, as such combinations may conflict with the ballast in terms of either the physical centration or orientation effects of the ballast and/or the optical effects of the combination. The various embodiments herein solve those issues by making sub-surface phase changes that may be tailored to the specific optical and physical properties of the lens, e.g. combinations of toric or cylindrical subsurface refractive index change corrections with diffractive multifocal patterns utilizing refractive index changes, all within a ballasted contact lens to maintain proper orientation to the eye. Using IRIS to correct the optical effects of the ballast may allow for more flexibility in optical zone size.

The outer edges of contact lenses and intraocular lenses often have specific physical requirements and optical effects. For example, the thickness of a contact lens can have implications for comfort or stability of the contact lens. For intraocular lenses, the peripheral edge is often configured to be square to help inhibit posterior capsule opacification, and/or it may include a shape or curvature to try to minimize reflections or scattering of light that may cause dysphotopsias. In each of these examples, the mechanical shape and/or thickness at the edge may have unwanted optical effects, such as edge reflections, reduced peripheral visual acuity, aberrations, halos, glare, scattering and other negative effects. In some embodiments, these unwanted edge effects may be counteracted or minimized by creating counteracting subsurface patterns within the lens at or near the edge via laser induced refractive index change, to counteract glare, halo, edge effects or dysphotopsias. For example, for a thin contact lens edge to maintain comfort and avoid excessive movement during blinking, the optical power required of the lens could be maintained across the entirety of the lens even out to the edge by adding optical power with laser induced refractive index change in the periphery. As another example in sharp edged IOLs, a laser induced refractive index GRIN layer could be added to the lens inside the periphery of the lens near the sharp edges to redirect peripheral light rays to bend outward to exit through the edge in a direction calculated not to cause glare or halo effects, for example by making the periphery to have a low or decreasing refractive index—e.g. decreasing with increasing distance from the optical axis of the lens. Further, the refractive index could be reduced to at or near the refractive index of the surrounding aqueous fluid in order to reduce internal reflections inside the lens that cause glare or halo.

While specific embodiment have been set forth in detail above, those skilled in the art who have reviewed the present disclosure will readily appreciate that other embodiments can be realized within the scope of the invention. For example, numerical values are illustrative rather than limiting, as are recitations of specific equipment and sources. While embodiments have been disclosed in terms of two-photon absorption, such embodiments can be implemented similarly through absorption of three or more photons. Therefore, the present invention should be construed as limited only by the appended claims.

We claim:

1. A method for providing an intraocular telescope lens system in an eye, comprising:
    providing a negative power lens element in the eye by (i) inserting an intraocular lens comprising a negative power lens element in the eye, or (ii) modifying the refractive index of crystalline lens tissue of the eye by irradiating select regions of the crystalline lens tissue with a focused, visible or near-IR laser below the optical breakdown threshold of the crystalline lens tissue to form a negative power lens element in the crystalline lens that exhibits a change in refractive index relative to non-irradiated crystalline lens tissue, and exhibits little or no scattering loss, and scanning over the select regions with the laser such that ablation or removal of the tissue is not observed in the irradiated region, and
    modifying the refractive index of cornea tissue of the eye by irradiating select regions of the cornea tissue with a focused, visible or near-IR laser below the optical breakdown threshold of the cornea tissue to provide a positive power lens element in the cornea that exhibits a change in refractive index relative to non-irradiated cornea tissue, and exhibits little or no scattering loss, and scanning over the select regions with the laser such that ablation or removal of the tissue is not observed in the irradiated region, and
    wherein the negative and positive power lens elements are aligned along an optical axis in the eye.

2. The method of claim 1, wherein the negative power lens element is provided by modifying the refractive index of crystalline lens tissue of the eye by irradiating select regions of the crystalline lens tissue with a focused, visible or near-IR laser below the optical breakdown threshold of the crystalline lens tissue to provide a negative power lens element in the crystalline lens that exhibits a change in refractive index relative to non-irradiated crystalline lens tissue, and exhibits little or no scattering loss, and scanning over the select regions with the laser such that ablation or removal of the tissue is not observed in the irradiated region.

3. The method of claim 1, wherein the negative power lens element is provided by inserting an intraocular lens comprising a negative power lens element in the eye.

4. The method of claim 1, wherein the focused, visible or near-IR laser has a pulse energy from 0.01 nJ to 10 nJ.

5. The method of claim 1, further comprises applying a multiple-photon-absorbing chromophore to the crystalline lens tissue or cornea tissue prior to modifying the refractive index of the crystalline lens tissue or cornea tissue.

6. The method of claim 5, wherein the multiple-photon-absorbing chromophore comprises a two-photon-absorbing chromophore.

7. The method of claim 1, wherein the laser emits pulses at a frequency between 1 MHz and 10 GHz.

8. The method of claim 7, wherein the laser frequency is between 10 MHz and 500 MHz.

9. The method of claim 1, wherein the laser has a pulse width between 10 fs and 100 fs.

10. The method of claim 1, wherein the laser pulses have an average power between 1 mW and 1,000 mW.

11. The method of claim 1, wherein the laser pulses have a pulse energy between 0.01 nJ and 10 nJ.

12. The method of claim 11, wherein the laser pulses have a pulse energy between 0.1 and 2 nJ.

13. The method of claim 1, wherein the focus spot is scanned at a scanning speed of at least 100 mm/s.

14. The method of claim 1, wherein the laser pulses have a wavelength between 600 and 1,000 nm.

15. The method of claim 1, wherein the laser pulses have a wavelength between 1,000 and 1,300 nm.

16. The method of claim 1, wherein the laser pulses have a wavelength between 350 and 600 nm.

17. The method of claim 1 wherein the provided positive power lens element in the cornea comprises a laser-modified GRIN layer.

18. The method of claim 1, wherein the provided positive power lens element in the cornea comprises an element selected from the group consisting of Bragg gratings, microlens arrays, zone plates, and Fresnel lenses.

* * * * *